US011141600B2

(12) United States Patent
Kaib et al.

(10) Patent No.: US 11,141,600 B2
(45) Date of Patent: *Oct. 12, 2021

(54) WATER RESISTANT WEARABLE MEDICAL DEVICE

(71) Applicant: ZOLL Medical Corporation, Chelmsford, MA (US)

(72) Inventors: Thomas E Kaib, Irwin, PA (US); Shane S Volpe, Saltsburg, PA (US); John G Clark, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 157 days.

This patent is subject to a terminal disclaimer.

(21) Appl. No.: 16/549,571

(22) Filed: Aug. 23, 2019

(65) Prior Publication Data

US 2019/0374784 A1 Dec. 12, 2019

Related U.S. Application Data

(60) Continuation of application No. 15/918,542, filed on Mar. 12, 2018, now Pat. No. 10,463,867, which is a
(Continued)

(51) Int. Cl.
*A61N 1/39* (2006.01)
*A61N 1/04* (2006.01)

(52) U.S. Cl.
CPC .......... *A61N 1/3968* (2013.01); *A61N 1/046* (2013.01); *A61N 1/0476* (2013.01);
(Continued)

(58) Field of Classification Search
CPC .... A61N 1/0476; A61N 1/046; A61N 1/3968; A61N 1/3925
See application file for complete search history.

(56) References Cited

U.S. PATENT DOCUMENTS 4,094,310 A 6/1978 McEachern et al.
4,432,368 A 2/1984 Russek
(Continued)

FOREIGN PATENT DOCUMENTS

CN 101031334 9/2007
CN 101657229 2/2010
(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.
(Continued)

*Primary Examiner* — Alyssa M Alter
(74) *Attorney, Agent, or Firm* — Zoll Medical Corporation

(57) ABSTRACT

A wearable medical device includes a water-resistant harness, and a plurality of ECG sensing electrodes and a plurality of therapy electrodes disposed on the harness. The plurality of therapy electrodes are configured to provide at least one defibrillating biphasic shock. The device includes a control unit comprised within a waterproof case. The control unit is configured to monitor ECG information of the patient based on a sensed ECG signal, and responsive to detection of a cardiac arrhythmia, provide the at least one defibrillating biphasic shock. The device includes a water-resistant or waterproof connection pod configured to electrically couple to the plurality of ECG sensing electrodes, the plurality of therapy electrodes, and the control unit, and to provide the sensed ECG signal from the plurality of ECG sensing electrodes to the control unit and the at least one defibrillating biphasic shock from the control unit to the plurality of therapy electrodes.

20 Claims, 14 Drawing Sheets

Related U.S. Application Data continuation of application No. 15/791,686, filed on Oct. 24, 2017, now Pat. No. 10,130,823, which is a continuation of application No. 15/295,726, filed on Oct. 17, 2016, now Pat. No. 9,827,434, which is a continuation of application No. 14/703,996, filed on May 5, 2015, now abandoned, which is a division of application No. 13/311,427, filed on Dec. 5, 2011, now Pat. No. 9,427,564.

(60) Provisional application No. 61/423,874, filed on Dec. 16, 2010.

(52) U.S. Cl.
CPC ......... *A61N 1/0484* (2013.01); *A61N 1/3987* (2013.01); *A61N 1/3993* (2013.01); *A61N 1/3925* (2013.01)

(56) References Cited

U.S. PATENT DOCUMENTS

| | | |
|---|---|---|
| 4,632,122 A | 12/1986 | Johansson et al. |
| 4,698,848 A | 10/1987 | Buckley |
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,176,380 A | 1/1993 | Evans et al. |
| 5,330,505 A | 7/1994 | Cohen |
| 5,348,008 A | 9/1994 | Bomn et al. |
| 5,353,793 A | 10/1994 | Bomn |
| 5,357,696 A | 10/1994 | Gray et al. |
| 5,365,932 A | 11/1994 | Greenhut |
| 5,472,453 A | 12/1995 | Alt |
| 5,544,661 A | 8/1996 | Davis et al. |
| 5,564,429 A | 10/1996 | Bomn et al. |
| 5,662,689 A | 9/1997 | Elsberry et al. |
| 5,716,380 A | 2/1998 | Yerkovich et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,406,426 B1 | 6/2002 | Reuss et al. |
| 6,666,830 B1 | 12/2003 | Lehrman et al. |
| 6,681,003 B2 | 1/2004 | Linder et al. |
| 6,690,969 B2 | 2/2004 | Bystrom et al. |
| 6,790,178 B1 | 9/2004 | Mault et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,908,437 B2 | 6/2005 | Bardy |
| 6,944,498 B2 | 9/2005 | Owen et al. |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,177,684 B1 | 2/2007 | Kroll et al. |
| 7,220,235 B2 | 5/2007 | Geheb et al. |
| 7,277,752 B2 | 10/2007 | Matos |
| 7,295,871 B2 | 11/2007 | Halperin et al. |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,702,390 B1 | 4/2010 | Min |
| 7,810,172 B2 | 10/2010 | Williams |
| 7,831,303 B2 | 11/2010 | Rueter et al. |
| 7,974,689 B2 | 7/2011 | Volpe et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,600,486 B2 | 12/2013 | Kaib et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,904,214 B2 | 12/2014 | Volpe et al. |
| 8,909,335 B2 | 12/2014 | Radzelovage |
| 9,008,801 B2 | 4/2015 | Kaib et al. |
| 9,135,398 B2 | 9/2015 | Kaib et al. |
| 9,186,089 B2 | 11/2015 | Mazar et al. |
| 9,283,399 B2 | 3/2016 | Donnelly et al. |
| 9,398,859 B2 | 7/2016 | Volpe et al. |
| 9,427,564 B2 | 8/2016 | Kaib et al. |
| 9,579,516 B2 | 2/2017 | Kaib et al. |
| 9,737,262 B2 | 8/2017 | Donnelly et al. |
| 9,782,578 B2 | 10/2017 | Kaib et al. |
| 9,827,434 B2 * | 11/2017 | Kaib .................. A61N 1/3968 |
| 9,937,355 B2 | 4/2018 | Kaib et al. |
| 9,955,938 B2 | 5/2018 | Herken et al. |
| 10,130,823 B2 | 11/2018 | Kaib et al. |
| 10,271,791 B2 | 4/2019 | Donnelly et al. |
| 10,463,867 B2 * | 11/2019 | Kaib .................. A61N 1/3968 |
| 10,582,858 B2 | 3/2020 | Volpe et al. |
| 2002/0107435 A1 | 8/2002 | Swetlik et al. |
| 2003/0004547 A1 | 1/2003 | Owen et al. |
| 2003/0023277 A1 | 1/2003 | Owen et al. |
| 2003/0032988 A1 | 2/2003 | Fincke |
| 2003/0055460 A1 | 3/2003 | Owen et al. |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2003/0233129 A1 | 12/2003 | Matos |
| 2004/0007970 A1 | 1/2004 | Ma et al. |
| 2004/0049233 A1 | 3/2004 | Edwards |
| 2004/0143297 A1 | 7/2004 | Ramsey, III |
| 2005/0049515 A1 | 3/2005 | Misczynski et al. |
| 2005/0131465 A1 | 6/2005 | Freeman et al. |
| 2006/0017575 A1 | 1/2006 | McAdams |
| 2006/0036292 A1 | 2/2006 | Smith et al. |
| 2006/0085049 A1 | 4/2006 | Cory et al. |
| 2006/0129067 A1 | 6/2006 | Grajales et al. |
| 2006/0178706 A1 | 8/2006 | Lisogurski et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2007/0299474 A1 | 12/2007 | Brink |
| 2008/0004536 A1 | 1/2008 | Baxi et al. |
| 2008/0015454 A1 | 1/2008 | Gal |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0221631 A1 | 9/2008 | Dupelle |

(56) References Cited

U.S. PATENT DOCUMENTS

| | | |
|---|---|---|
| 2008/0249591 A1 | 10/2008 | Gaw et al. |
| 2008/0287770 A1 | 11/2008 | Kurzweil et al. |
| 2008/0306560 A1 | 12/2008 | Macho et al. |
| 2008/0306562 A1 | 12/2008 | Donnelly et al. |
| 2008/0312520 A1 | 12/2008 | Rowlandson et al. |
| 2008/0312709 A1 | 12/2008 | Volpe et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0082691 A1 | 3/2009 | Denison et al. |
| 2009/0093687 A1 | 4/2009 | Telfort et al. |
| 2009/0138059 A1 | 5/2009 | Ouwerkerk |
| 2009/0177100 A1 | 7/2009 | Ternes |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0083968 A1 | 4/2010 | Wondka et al. |
| 2010/0179438 A1 | 7/2010 | Heneghan et al. |
| 2010/0234715 A1 | 9/2010 | Shin et al. |
| 2010/0234716 A1 | 9/2010 | Engel |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0077728 A1 | 3/2011 | Li et al. |
| 2011/0196220 A1 | 8/2011 | Storm |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0144551 A1 | 6/2012 | Guldalian |
| 2012/0146797 A1 | 6/2012 | Oskin et al. |
| 2012/0150008 A1 | 6/2012 | Kaib et al. |
| 2012/0158074 A1 | 6/2012 | Hall |
| 2012/0158075 A1 | 6/2012 | Kaib et al. |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0371806 A1 | 12/2014 | Raymond et al. |
| 2015/0005588 A1 | 1/2015 | Kaib |
| 2015/0039053 A1 | 2/2015 | Kaib et al. |
| 2015/0217121 A1 | 8/2015 | Subramanian et al. |
| 2015/0231403 A1 | 8/2015 | Kaib et al. |
| 2016/0143585 A1 | 5/2016 | Donnelly et al. |
| 2016/0296125 A1 | 10/2016 | Volpe et al. |
| 2017/0143977 A1 | 5/2017 | Kaib et al. |

FOREIGN PATENT DOCUMENTS

| | | |
|---|---|---|
| CN | 101848677 | 9/2010 |
| DE | 2644236 | 4/1981 |
| EP | 0295497 | 9/1993 |
| EP | 1642616 | 4/2006 |
| EP | 1455640 | 1/2008 |
| EP | 1720446 | 7/2010 |
| EP | 0335356 | 3/2016 |
| JP | S6368135 | 3/1988 |
| JP | 5115450 | 5/1993 |
| JP | H10-28679 | 2/1998 |
| JP | H111319119 | 11/1999 |
| JP | 2002102361 | 4/2002 |
| JP | 2002514107 | 5/2002 |
| JP | 2002200059 | 7/2002 |
| JP | 2002534231 | 10/2002 |
| JP | 2004538066 | 12/2004 |
| JP | 2006136707 | 6/2006 |
| JP | 2007531592 | 11/2007 |
| JP | 2008302228 | 12/2008 |
| JP | 2009510276 | 3/2009 |
| JP | 2009518057 | 5/2009 |
| JP | 2010508128 | 3/2010 |
| JP | 2010530114 | 9/2010 |
| WO | 200002484 | 1/2000 |
| WO | 2004054656 | 7/2004 |
| WO | 2004067083 | 8/2004 |
| WO | 2005082454 | 9/2005 |
| WO | 2006050235 | 5/2006 |
| WO | 2007019325 | 2/2007 |
| WO | 20070057169 | 5/2007 |
| WO | 2007077997 | 7/2007 |
| WO | 2008137286 | 11/2008 |
| WO | 2009034506 | 3/2009 |
| WO | 2010014497 | 2/2010 |
| WO | 2010025432 | 3/2010 |
| WO | 2015127466 | 8/2015 |

OTHER PUBLICATIONS

DeBock et al., "Captopril treatment of chronic heart failure in the very old," J. Gerontol. (1994) 49: M148-M152.

Harnett, P.R. et al., "A Survey and Comparison of Laboratory Test Methods for Measuring Wicking", Textile Research Journal, Jul. 1984.

Notification of Transmittal of the International Search Report and the Written Opinion of the International Searching Authority, dated Apr. 19, 2012 for International Application No. PCT/US2011/064138.

O'Keeffe et al., "Reproducability and responsiveness of quality of life assessment and six minute walk test in elderly heart failure patients," Heart (1998) 80: 377-382.

Extended European Search Report from corresponding European Application No. 19208852.4 dated Mar. 5, 2020.

* cited by examiner

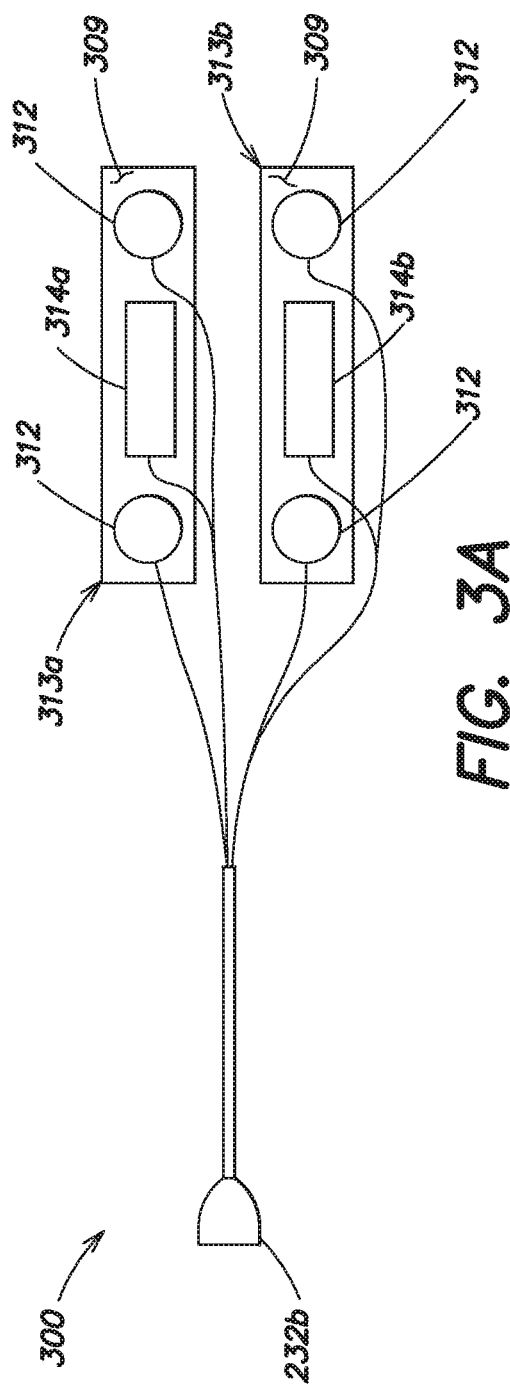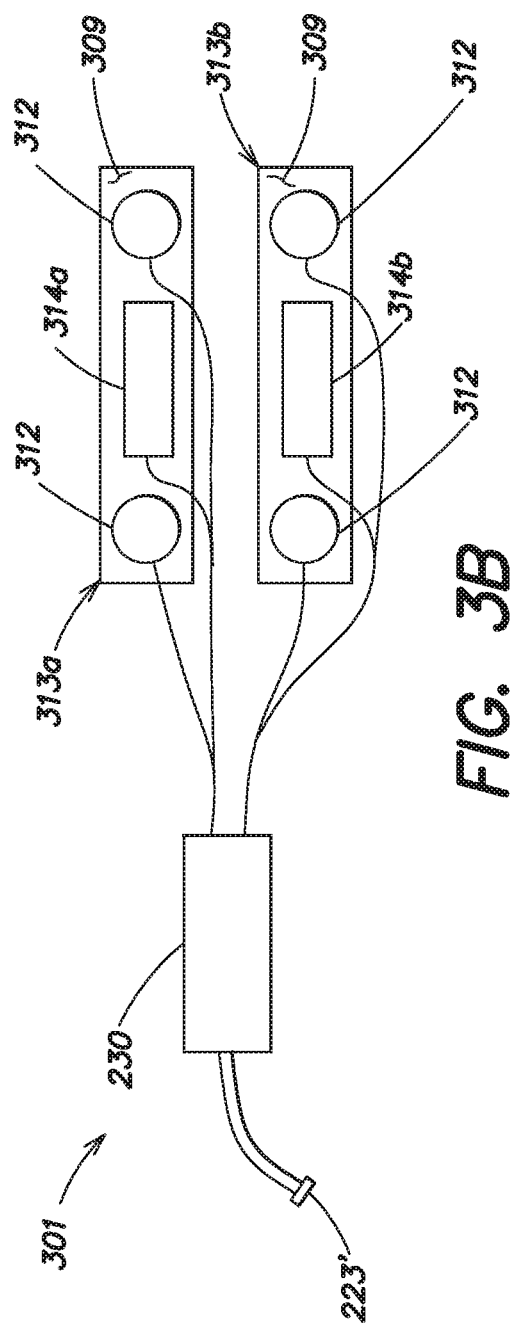
FIG. 3A
FIG. 3B

WATER RESISTANT WEARABLE MEDICAL DEVICE

CROSS REFERENCE TO RELATED APPLICATIONS

This application claims the benefit under 35 U.S.C. § 120 as a continuation of U.S. application Ser. No. 15/918,542, filed Mar. 12, 2018 and titled "WATER RESISTANT WEARABLE MEDICAL DEVICE," which is incorporated herein by reference in its entirety. U.S. application Ser. No. 15/918,542 claims the benefit under 35 U.S.C. § 120 as a continuation of U.S. application Ser. No. 15/791,686, filed Oct. 24, 2017 and titled "WATER RESISTANT WEARABLE MEDICAL DEVICE", now U.S. Pat. No. 10,130,823, which is incorporated herein by reference in its entirety. U.S. application Ser. No. 15/791,686 claims the benefit under 35 U.S.C. § 120 as a continuation of U.S. application Ser. No. 15/295,726, filed Oct. 17, 2016 and titled "WATER RESISTANT WEARABLE MEDICAL DEVICE", now U.S. Pat. No. 9,827,434, which is incorporated herein by reference in its entirety. U.S. application Ser. No. 15/295,726 claims the benefit under 35 U.S.C. § 120 as a continuation of U.S. application Ser. No. 14/703,996, filed May 5, 2015 and titled "WATER RESISTANT WEARABLE MEDICAL DEVICE" which is incorporated herein by reference in its entirety. U.S. application Ser. No. 14/703,996 claims the benefit under 35 U.S.C. § 121 as a division of U.S. application Ser. No. 13/311,427, filed Dec. 5, 2011 and titled "WATER RESISTANT WEARABLE MEDICAL DEVICE", now U.S. Pat. No. 9,427,564, which is incorporated herein by reference in its entirety. U.S. application Ser. No. 13/311,427 claims priority under 35 U.S.C. § 119(e) to U.S. Provisional Application Ser. No. 61/423,874 titled "WATER RESISTANT WEARABLE MEDICAL DEVICE," filed Dec. 16, 2010, which is incorporated herein by reference in its entirety.

BACKGROUND OF THE INVENTION

1. Field of the Invention

The present invention is directed to a water resistant and/or waterproof wearable medical device, such as a defibrillator.

2. Discussion of Related Art

Cardiac arrest and other cardiac health ailments are a major cause of death worldwide. Various resuscitation efforts aim to maintain the body's circulatory and respiratory systems during cardiac arrest in an attempt to save the life of the victim.

The sooner these resuscitation efforts begin, the better the victim's chances of survival. These efforts are expensive and have a limited success rate, and cardiac arrest, among other conditions, continues to claim the lives of victims.

To protect against cardiac arrest and other cardiac health ailments, some at-risk patients may use a wearable defibrillator, such as the LifeVest® wearable cardioverter defibrillator available from Zoll Medical Corporation of Chelmsford, Mass. To remain protected, the patient wears the device nearly continuously while going about their normal daily activities, while awake, and while asleep.

SUMMARY OF THE INVENTION

In accordance with one aspect, a wearable medical device is provided. The wearable medical device includes a water-resistant or waterproof housing configured to be continuously or nearly continuously worn by a patient, the water-resistant or waterproof housing formed from a water-resistant or waterproof material and configured to prevent ingress of water during operation of the wearable medical device in a wet environment. The wearable medical device further includes a plurality of ECG sensing electrodes configured to be removably coupled to the patient and configured to monitor an ECG of the patient during operation of the wearable medical device. The wearable medical device further includes a plurality of therapy electrodes configured to be removably coupled to the patient and configured to deliver at least one therapeutic pulse to the patient. The wearable medical device further includes a control unit disposed within the water-resistant or waterproof housing and configured to be electrically coupled to the plurality of ECG sensing electrodes and the plurality of therapy electrodes. The control unit is configured to receive the monitored ECG of the patient, and responsive to detection of a cardiac arrhythmia based on the monitored ECG of the patient, provide the at least one therapeutic pulse to the patient via the at least one therapy electrode.

According to one embodiment, one or more of the plurality of ECG sensing electrodes comprises an adhesive to attach the respective one or more of the plurality of ECG sensing electrodes to a body of the patient. According to another embodiment, one or more of the plurality of therapy electrodes comprises an adhesive to attach the respective one or more of the plurality of therapy electrodes to a body of the patient. According to yet another embodiment, each of the plurality of therapy electrodes is of a sufficient dimension so as to be capable of delivering the at least one therapeutic pulse to a body of the patient.

According to one embodiment, the plurality of therapy electrodes comprises a first therapy electrode configured to be adhesively attached to a front of a torso of the patient and a second therapy electrode configured to be adhesively attached to a back of the torso of the patient. According to another embodiment, the plurality of therapy electrodes is configured to be applied to at least one of spaced-apart positions and opposing lateral sides of a torso of the patient. According to a further embodiment, the plurality of therapy electrodes comprises a first therapy electrode configured to be positioned substantially below a left breast of the patient and a second therapy electrode configured to be positioned substantially above a right breast of the patient.

According to another embodiment, the plurality of ECG sensing electrodes comprises two ECG sensing electrodes that are placed on either side of at least one of the plurality of therapy electrodes. According to another embodiment, the plurality of ECG sensing electrodes comprises at least three ECG sensing electrodes and the plurality of therapy electrodes comprises two therapy electrodes, and wherein each of the ECG sensing electrodes is disposed substantially adjacent a therapy electrode. In a further embodiment, the at least three ECG sensing electrodes and the plurality of therapy electrodes are configured to be positioned on a front of a torso of the patient.

According to one embodiment, a patient responsiveness button is provided and configured to allow the patient to indicate to the control unit that the patient is conscious in response to the detection of the cardiac arrhythmia. According to another embodiment, the plurality of ECG sensing electrodes and the plurality of therapy electrodes comprises at least one pair of combined ECG/therapy electrodes. According to a further embodiment, each of the at least one pair of combined ECG/therapy electrodes includes a pair of the ECG sensing electrodes and a single therapy electrode that are disposed on a common adhesive backing. According to still a further embodiment, a patient responsiveness button is configured to allow the patient to indicate to the control unit that the patient is conscious in response to the detection of the cardiac arrhythmia. In yet a further embodiment, the patient responsiveness button is disposed along with at least one pair of combined ECG/therapy electrodes of the at least one pair of combined ECG/therapy electrodes on a common adhesive backing.

According to another aspect, a wearable medical device is provided. The wearable medical device includes a water-resistant or waterproof housing configured to be continuously or nearly continuously worn by a patient, the water-resistant or waterproof housing formed from a water-resistant or waterproof material and configured to prevent ingress of water during operation of the wearable medical device in a wet environment. The wearable medical device further includes a plurality of ECG sensing electrodes configured to be removably coupled to the patient and configured to monitor an ECG of the patient during operation of the wearable medical device.

The wearable medical device further includes a plurality of therapy electrodes configured to be removably coupled to the patient and configured to deliver at least one therapeutic pulse to the patient, wherein one or more of the plurality of ECG sensing electrodes and the plurality of therapy electrodes comprises an adhesive for adhesively attaching the one or more of the plurality of ECG sensing electrodes and the plurality of therapy electrodes to the patient, and wherein the plurality of ECG sensing electrodes is configured to monitor the ECG of the patient during operation of the wearable medical device in the wet environment and the plurality of therapy electrodes is configured to deliver the at least one therapeutic pulse to the patient during the operation of the wearable medical device in the wet environment.

The wearable medical device further includes a control unit disposed within the water-resistant or waterproof housing and configured to be electrically coupled to the plurality of ECG sensing electrodes and the plurality of therapy electrodes, the control unit configured to receive the monitored ECG of the patient, and responsive to detection of a cardiac arrhythmia based on the monitored ECG of the patient, provide the at least one therapeutic pulse of energy to the patient via the at least one therapy electrode.

According to one embodiment, each of the plurality of therapy electrodes is of a sufficient dimension so as to be capable of delivering the at least one therapeutic pulse to a body of the patient. According to another embodiment, the plurality of therapy electrodes comprises a first therapy electrode configured to be adhesively attached to a front of a torso of the patient and a second therapy electrode configured to be adhesively attached to a back of the torso of the patient. According to yet another embodiment, the plurality of therapy electrodes is configured to be applied to at least one of spaced-apart positions and opposing lateral sides of a torso of the patient. According to a further embodiment, the plurality of therapy electrodes comprises a first therapy electrode configured to be positioned substantially below a left breast of the patient and a second therapy electrode configured to be positioned substantially above a right breast of the patient.

According to one embodiment, the plurality of ECG sensing electrodes comprises two ECG sensing electrodes that are placed on either side of at least one of the plurality of therapy electrodes. According to another embodiment, the plurality of ECG sensing electrodes comprises at least three ECG sensing electrodes and the plurality of therapy electrodes comprises two therapy electrodes, and wherein each of the ECG sensing electrodes is disposed substantially adjacent a therapy electrode. In a still further embodiment, the at least three ECG sensing electrodes and the plurality of therapy electrodes are configured to be positioned on a front of a torso of the patient.

According to another embodiment, a patient responsiveness button is provided and configured to allow the patient to indicate to the control unit that the patient is conscious in response to the detection of the cardiac arrhythmia. According to another embodiment, the plurality of ECG sensing electrodes and the plurality of therapy electrodes comprises at least one pair of combined ECG/therapy electrodes. According to a further embodiment, each of the at least one pair of combined ECG/therapy electrodes includes a pair of the ECG sensing electrodes and a single therapy electrode that are disposed on a common adhesive backing. According to yet a further embodiment, a patient responsiveness button is provided and configured to allow the patient to indicate to the control unit that the patient is conscious in response to the detection of the cardiac arrhythmia. According to a further embodiment, the patient responsiveness button is disposed along with a combined ECG/therapy electrode of the at least one pair of combined ECG/therapy electrodes on a common adhesive backing.

Still other aspects, embodiments, and advantages of these exemplary aspects and embodiments are discussed in detail below. Moreover, it is to be understood that both the foregoing information and the following detailed description are merely illustrative examples of various aspects and embodiments of the present invention, and are intended to provide an overview or framework for understanding the nature and character of the claimed aspects and embodiments. Any embodiment disclosed herein may be combined with any other embodiment in any manner consistent with at least one of the aspects disclosed herein, and references to "an embodiment," "some embodiments," "an alternate embodiment," "various embodiments," "one embodiment," "at least one embodiment," "this and other embodiments" or the like are not necessarily mutually exclusive and are intended to indicate that a particular feature, structure, or characteristic described in connection with the embodiment may be included in at least one embodiment. The appearance of such terms herein is not necessarily all referring to the same embodiment.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3a illustrates a combined ECG/therapy electrode system for use with the shower kit of FIG. 2a;

FIG. 3b illustrates a combined ECG/therapy electrode system for use with the shower kit of FIG. 2b;

DETAILED DESCRIPTION

Figure 1A:
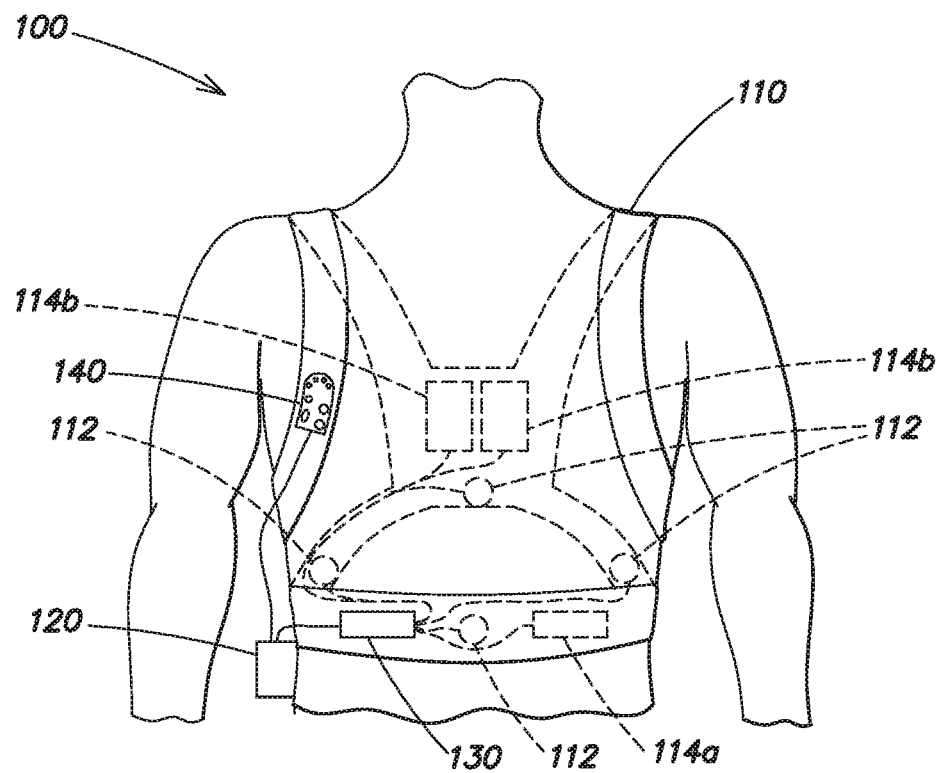
FIG. 1a illustrates a wearable medical device, such as a wearable defibrillator.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof as well as additional items.

As discussed above, to provide protection against cardiac arrest, patients that use a wearable medical device, such as a wearable defibrillator, generally wear the device nearly continuously while they are awake and while they are asleep. However, there are periods of time where it may not be possible or practical for them to wear the device, such as when taking a shower or bathing. During such times, the patient may remove the device when they get undressed to take a shower or bath, and may not put the device back on until they have finished showering or bathing and drying off. During this period of time, the patient is not protected. To minimize the amount of time in which they are not protected, many patients spend a minimal amount of time bathing. Further, because the patient is not protected when the device is removed from the patient's body, physicians typically recommend that someone remain with the patient when the device is removed, to render assistance in case of a medical emergency.

Applicants have appreciated there is need to protect patients at risk of cardiac arrest when they are showering or bathing, or even when swimming. To address this need, Applicants have developed a number of different embodiments of a wearable medical device, such as a wearable defibrillator, that are water resistant, waterproof, or are designed in a manner in which certain components of the wearable medical device that can be compromised by contact with water or another liquid can be placed in a dry location, yet still protect the patient.

FIG. 1a illustrates a wearable medical device, such as a LifeVest® Wearable Cardioverter Defibrillator available from Zoll Medical Corporation of Chelmsford, Mass. As shown, the wearable medical device 100 includes a harness 110 having a pair of shoulder straps and a belt that is worn about the torso of a patient. The harness 110 is typically made from a material, such as cotton, that is breathable, and unlikely to cause skin irritation, even when worn for prolonged periods of time. The wearable medical device 100 includes a plurality of ECG sensing electrodes 112 that are attached to the harness 110 at various positions about the patient's body and electrically coupled to a control unit 120 via a connection pod 130. The plurality of ECG sensing electrodes 112, which may be dry-sensing capacitance electrodes, are used by the control unit 120 to monitor the cardiac function of the patient and generally include a front/back pair of ECG sensing electrodes and a side/side pair of ECG sensing electrodes. It should be appreciated that additional ECG sensing electrodes may be provided, and the plurality of ECG sensing electrodes 112 may be disposed at varying locations about the patient's body.

The wearable medical device 100 also includes a plurality of therapy electrodes 114 that are electrically coupled to the control unit 120 via the connection pod 130 and which are capable of delivering one or more therapeutic defibrillating shocks to the body of the patient, if it is determined that such treatment is warranted. As shown, the plurality of therapy electrodes 114 includes a first therapy electrode 114a that is disposed on the front of the patient's torso and a second therapy electrode 114b that is disposed on the back of the patient's torso. The second therapy electrode 114b includes a pair of therapy electrodes that are electrically coupled together and act as the second therapy electrode 114b. The use of two therapy electrodes 114a, 114b permits a biphasic shock to be delivered to the body of the patient, such that a first of the two therapy electrodes can deliver a first phase of the biphasic shock with the other therapy electrode acting as a return, and the other therapy electrode can deliver the second phase of the biphasic shock with the first therapy electrode acting as the return. The connection pod 130 electrically couples the plurality of ECG sensing electrodes 112 and the plurality of therapy electrodes 114 to the control unit 120, and may include electronic circuitry. For example, in one implementation the connection pod 130 includes signal acquisition circuitry, such as a plurality of differential amplifiers to receive ECG signals from different ones of the plurality of ECG sensing electrodes 112 and to provide a differential ECG signal to the control unit 120 based on the difference therebetween. The connection pod 130 may also include other electronic circuitry, such as a motion sensor or accelerometer by which patient activity may be monitored.

As shown in FIG. 1a, the wearable medical device 100 may also include a user interface pod 140 that is electrically coupled to the control unit 120. The user interface pod 140 can be attached to the patient's clothing or to the harness 110, for example, via a clip (not shown) that is attached to a portion of the interface pod 140. Alternatively, the user interface pod 140 may simply be held in a person's hand. The user interface pod 140 typically includes one or more buttons by which the patient, or a bystander can communicate with the control unit 120, and a speaker by which the control unit 120 may communicate with the patient or the bystander. In certain models of the LifeVest® Wearable Cardioverter Defibrillator, the functionality of the user interface pod 140 is incorporated into the control unit 120.

Where the control unit 120 determines that the patient is experiencing cardiac arrhythmia, the control unit 120 may issue an audible alarm via a loudspeaker (not shown) on the control unit 120 and/or the user interface pod 140 alerting the patient and any bystanders to the patient's medical condition. The control unit 120 may also instruct the patient to press and hold one or more buttons on the control unit 120 or on the user interface pod 140 to indicate that the patient is conscious, thereby instructing the control unit 120 to withhold the delivery of one or more therapeutic defibrillating shocks. If the patient does not respond, the device may presume that the patient is unconscious, and proceed with the treatment sequence, culminating in the delivery of one or more defibrillating shocks to the body of the patient.

The control unit 120 generally includes at least one processor, microprocessor, or controller, such as a processor commercially available from companies such as Texas Instruments, Intel, AMD, Sun, IBM, Motorola, Freescale and ARM Holdings. In one implementation, the at least one processor includes a power conserving processor arrangement that comprises a general purpose processor, such as an Intel® PXA270 processor and a special purpose processor, such as a Freescale™ DSP56311 Digital Signal Processor. Such a power conserving processor arrangement is described in co-pending application Ser. No. 12/833,096, entitled SYSTEM AND METHOD FOR CONSERVING POWER IN A MEDICAL DEVICE, filed Jul. 9, 2010 (hereinafter the "'096 application") which is incorporated by reference herein in its entirety. The at least one processor of the control unit 120 is configured to monitor the patient's medical condition, to perform medical data logging and storage, and to provide medical treatment to the patient in response to a detected medical condition, such as cardiac arrhythmia.

Although not shown, the wearable medical device 100 may include additional sensors, other than the ECG sensing electrodes 112, capable of monitoring the physiological condition or activity of the patient. For example, sensors capable of measuring blood pressure, heart rate, heart sounds, thoracic impedance, pulse oxygen level, respiration rate, and the activity level of the patient may also be provided.

Figure 1B:
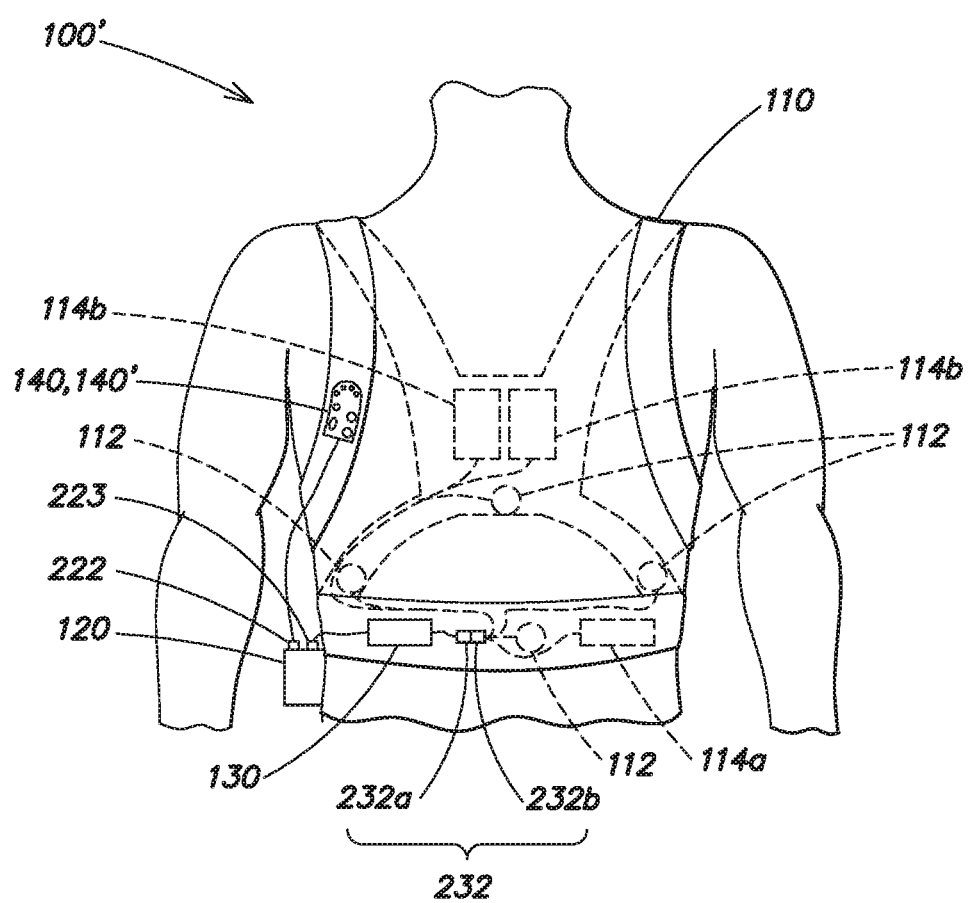
FIG. 1b illustrates a wearable medical device, such as a wearable defibrillator, in accordance with an embodiment of the present invention.

FIG. 1b illustrates a wearable medical device, such as a wearable defibrillator in accordance with an embodiment of the present invention. The wearable medical device 100' is generally similar in both form and function to the wearable medical device 100 described with respect to FIG. 1a, and thus only the differences between the wearable medical device 100' of FIG. 1b and the wearable medical device 100 of FIG. 1a are described in detail herein. In accordance with a first embodiment, the user interface pod 140 is electrically coupled to the control unit 120 via a removable connector 222 shown more clearly in FIG. 2a (described in detail further below), and the connection pod 130 is electrically coupled to the plurality of ECG sensing electrodes 112 and the plurality of therapy electrodes 114 via a removable and water-resistant or waterproof connector 232. In this first embodiment, the removable connector 222 permits the user interface pod 140 to be disconnected and reconnected to the control unit 120. The connector 232 includes two mating portions 232a and 232b that permit the connection pod 130 to be separated from and re-attached to the harness 110, the plurality of ECG sensing electrodes 112, and the plurality of therapy electrodes 114. As described more fully below with respect to FIG. 2a, in this first embodiment, where the patient desires to shower or bathe, they may disconnect the user interface pod 140 from the control unit 120, disconnect the connection pod 130 from the harness 110, the plurality of ECG sensing electrode 112, and the plurality of therapy electrodes 114, and remove the harness 110. The patient may then reconnect the user interface pod 140 to the control unit 120 and reconnect the connection pod 130 to a plurality of ECG sensing electrodes 212 and a plurality of therapy electrodes 214 associated with a shower kit 200.

In accordance with an alternative second embodiment, both the user interface pod 140 and the connection pod 130 are electrically coupled to the control unit 120 via removable connectors 222, 223, respectively. In this second embodiment, the connector 232 is not present and the plurality of ECG sensing electrodes 112 and the plurality of therapy electrodes 114 are directly connected to the connection pod 130. The removable connectors 222, 223 permit the user interface pod 140 and the connection pod 130 to be disconnected and reconnected to the control unit 120. As described more fully below with respect to FIG. 2b, in this second embodiment, where the patient desires to shower or bathe, they may disconnect the user interface pod 140 and the connection pod 130 from the control unit 120, remove the harness 110, and reconnect the control unit 120 to the user interface pod 140 and to a connection pod 230 and a plurality of ECG sensing electrodes 212 and a plurality of therapy electrodes 214 associated with a shower kit 200'.

Figure 2A:
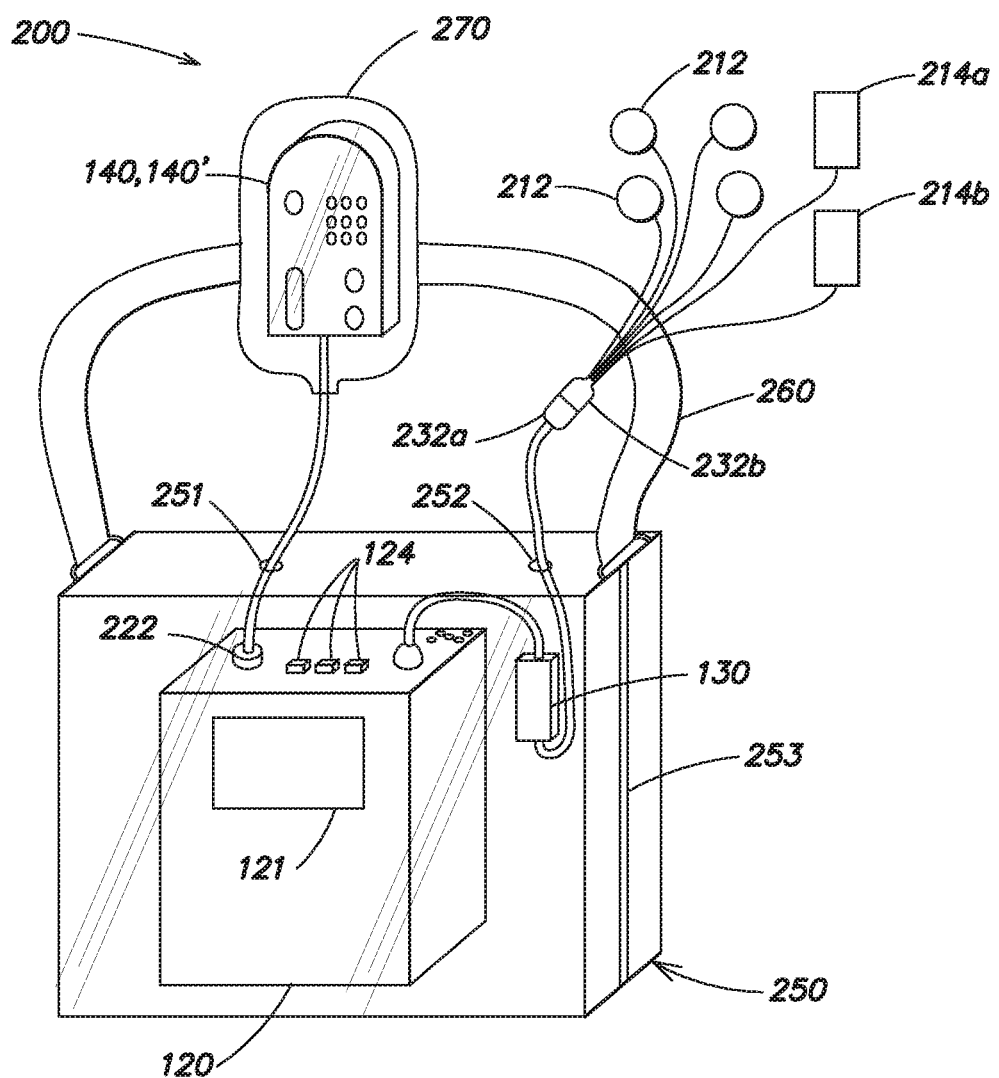
FIG. 2a illustrates a shower kit that may be used with the wearable medical device of FIG. 1b in accordance with an embodiment of the present invention.

FIG. 2a illustrates a shower kit 200 that may be used with a wearable medical device, such as the wearable medical device 100' depicted in FIG. 1b to permit a patient to shower or bathe while remaining protected from possibility of cardiac arrest. As illustrated in FIG. 2a, the shower kit 200 includes a waterproof or water-resistant enclosure 250 configured to receive the control unit 120 and the connection pod 130. The enclosure 250 includes a water resistant closure 253 which can be opened and sealed and through which the control unit 120 and the connection pod 130 may be inserted into and removed from the enclosure 250. The water resistant closure 253 may be a press and seal closure, similar to that of a Ziploc® seal plastic bag, a water-resistant zipper, a roll-top closure, or even an elastic ring, such as a conventional elastic band, as the present invention is not limited to any particular type of closure. Enclosure 250 includes a first aperture 251 through which the removable connector 222 may be inserted to electrically couple to user interface pod 140 to the control unit 120, and a second aperture 252 through which the mating portion 232a of the removable connector 232 may be passed through and connected to mating portion 232b. The first and second apertures 251 and 252 may be surrounded by an elastomeric seal that conforms to the diameter of the cable passed therethrough to prevent the ingress of water into the enclosure 250. In one embodiment, the enclosure 250 is formed from a transparent, flexible and water-resistant material, such as a clear plastic, although other suitable materials may be used. The use of a transparent flexible material permits the patient to access any buttons 124 present on the control unit 120, and permits the patient to view any messages that may be provided on a display 121 of the control unit 120. The enclosure 250 may include a strap 260 that is attached to the enclosure 250 to permit the enclosure (with control unit and connection pod 130 sealed therein) to be worn on the patient's body during bathing, or alternatively, to be hung on a hook.

The shower kit 200 also includes an enclosure 270 in which the user interface pod 140 can be received and protected from moisture, where the user interface pod 140 is not itself water-resistant. The enclosure 270 may be formed from a transparent flexible material, such as plastic, that permits the patient to view and access any buttons present on the user interface pod 140. The enclosure 270 may include a water resistant closure (not shown) to prevent any ingress of moisture. Alternatively, the enclosure 270 may be sealed with tape or an elastic band. Where the wearable medical device 100' includes a user interface pod 140' that is water-resistant or waterproof, the use of the enclosure 270 may be omitted. Similarly, where the functionality of the user interface pod 140 is integrated into the control unit 120, such as in the LifeVest® model 4000 Wearable Cardioverter Defibrillator, the enclosure 250 may include only a single aperture (i.e., the second aperture 252 through which the mating portion 232a of the removable connector is passed and connected to mating portion 232b).

As shown in FIG. 2a, the shower kit 200 also includes a plurality of ECG sensing electrodes 212 and a plurality of therapy electrodes 214 that are electrically coupled to the mating portion 232b of the waterproof or water-resistant connector 232. In accordance with an aspect of the present invention, each of the plurality of ECG sensing electrodes 212 may be conventional ECG electrodes with an adhesive backing that are simply directly attached to the body of the patient. Similarly, the plurality of therapy electrodes 214 may also be conventional adhesively backed electrodes that are of a sufficient dimension so as to be capable of delivering one or more defibrillating pulses of energy to the body of the patient. The plurality of therapy electrodes 214 includes a first therapy electrode 214a that can be adhesively attached to the front of the patient's torso, and a second therapy electrode that can be adhesively attached to the back of the patient's torso 214b. It should be appreciated that because it may be difficult for the patient themselves to attach the second therapy electrode 214b to the back of their torso, the plurality of therapy electrodes 214 may also be placed on the front of the patient's torso at spaced apart positions, or on opposing lateral sides of the patient's torso. For example, the first therapy electrode 214a may be placed so that it is positioned below and approximately centered on the patient's left breast, and the second therapy electrode may be placed so that it is positioned above and approximately centered on the patient's right breast. The plurality of ECG sensing electrodes 212 could also be placed on the front of the patient's torso with an ECG sensing electrode positioned on each side of a respective therapy electrode 214a, 214b. Other placements of the plurality of ECG sensing electrodes 212 and the plurality of therapy electrodes 214 may also be used.

In accordance with an aspect of the present invention, during those times where the patient is not bathing, the patient may wear the wearable medical device 100' illustrated in FIG. 1b while awake and while asleep. When it is necessary or desirable to bathe, the patient may use the shower kit 200 in the following manner to minimize the amount of time during which they are not protected from cardiac arrest.

When the patient decides to bathe, the patient removes their clothing, disconnects the connector 222 from the control unit 120 and disconnects the plurality of ECG sensing electrodes 112 and the plurality of therapy electrodes 114 from the removable connector 232 and removes the connection pod 130 from the harness 110. The patient may then remove the harness 110, insert the control unit 120 into the enclosure 250, push the connector 222 through the aperture 251 in the enclosure and electrically couple it to the control unit 120. The patient may then push the mating portion 232a through the aperture 252 in the enclosure 250 and connect the mating portion 232a to the mating portion 232b so that the connection pod 130 is electrically coupled to the plurality of ECG sensing electrodes 212 and the plurality of therapy electrodes 214. The patient would then typically attach the plurality of ECG sensing electrodes 212 to the front and back and sides of their body, and then attach the therapy electrodes 214a and 214b to the front and back of their body. Although the exact location of the electrodes 212, 214 may vary, they may generally be attached to the patient's body in locations similar to those of the wearable medical device 100'. Where placement of electrodes 212, 214 in locations similar to those of the wearable medical device 100' is not practical or possible (e.g., due to the dexterity of the patient, or due to the lack of an available caretaker to assist in the attachment of the electrodes 212, 214), the electrodes 212, 214 may be placed in other locations about the patient's body. For example, as discussed previously above the therapy electrodes 214 may be attached to opposing sides of anterior of the patient's body (e.g., below the patient's left breast and above the patient's right breast) with an ECG sensing electrode 212 attached on each side of a therapy electrode. It should be appreciated that in other embodiments, only two ECG sensing electrodes 212 may be provided.

Depending upon whether a water resistant user interface pod 140' or a non-water resistant user interface pod 140 was used, the patient may place the non-water resistant user interface pod 140 into the enclosure 270 and seal the enclosure. Where the functionality of the user interface pod 140 is integrated into the control unit 120, this step may simply be omitted. The enclosure 250 may then be sealed and the patient is now ready to bathe. Because the patient is now protected, they may shower or bathe for as long as they would like, or as frequently as desired.

It should be appreciated that the various steps described above may be performed in an order different than that described above. For example, to further reduce the amount of time the patient is not protected, the patient may get undressed and place the electrodes 212, 214 on their body while the wearable medical device 100' and its associated harness 110 are still in position on the patient's body. It should be appreciated that the shower kit 200 provides the patient with protection against cardiac arrest while utilizing most of the components of the wearable medical device 100 of FIG. 1a with minimal modification, and with minimal added expense.

Figure 2B:
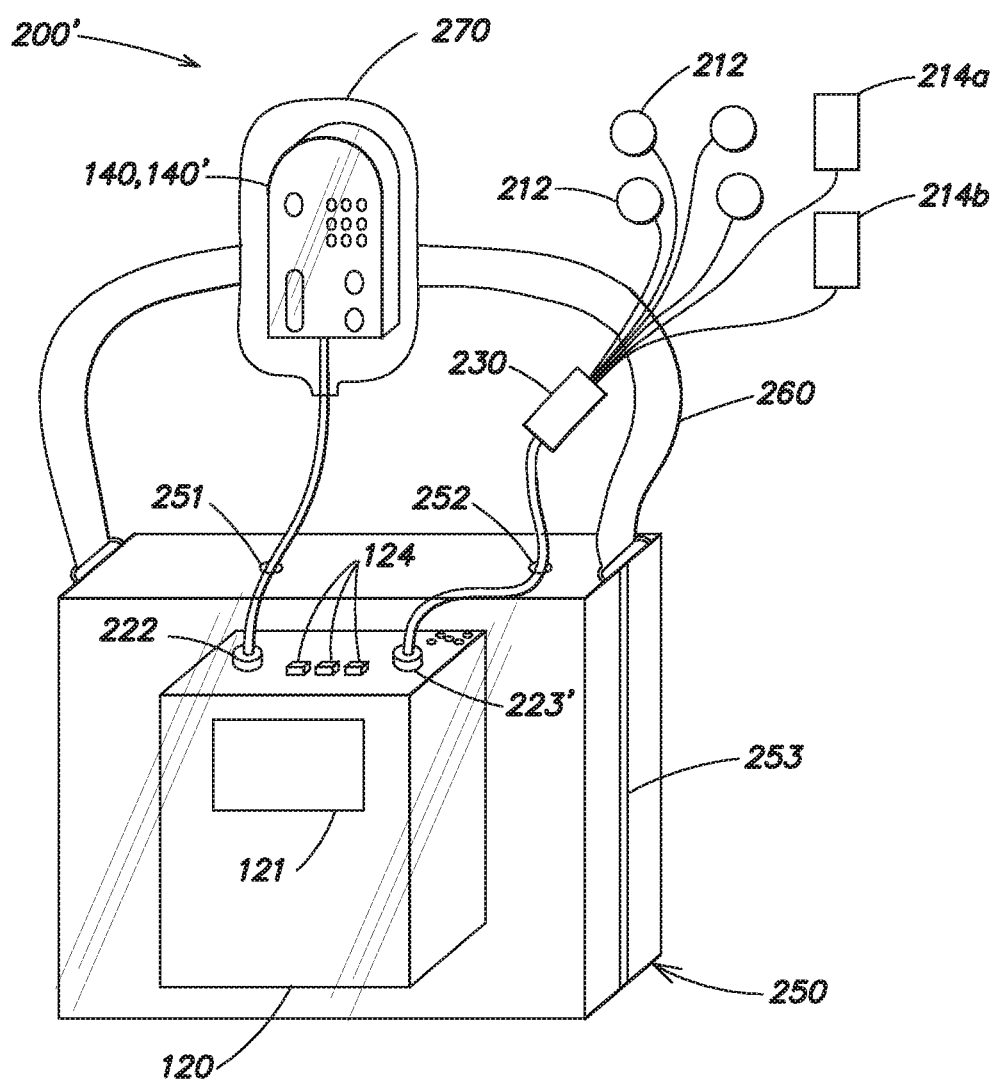
FIG. 2b illustrates a shower kit that may be used with the wearable medical device of FIG. 1b in accordance with another embodiment of the present invention.

FIG. 2b illustrates an alternative shower kit 200' that may be used with a wearable medical device, such as the wearable medical device 100' depicted in FIG. 1b, to permit a patient to shower or bathe while remaining protected from the possibility of cardiac arrest. As the shower kit 200' is similar to the shower kit 200 illustrated in FIG. 2a, only differences will be described in detail herein. As in the shower kit 200, the shower kit 200' includes a waterproof or water-resistant enclosure 250 that is configured to receive the control unit 120 and which includes a water resistant closure 253 which can be opened and sealed. The enclosure 250 may again be formed from a transparent, flexible material, such as plastic, that permits a patient to view and access portions of the control unit 120. However, in contrast to the embodiment of FIG. 2a, the shower kit 200' includes a connection pod 230 in addition to the plurality of ECG sensing electrodes and the plurality of therapy electrodes 214. The connection pod 230 is similar in function to the connection pod 130, and may include many of the same components, such as signal acquisition circuitry, motion sensors or accelerometers, etc. However, the connection pod 230 is specifically configured to be water resistant and/or waterproof. This may be achieved in a well known manner by sealing all openings in the connection pod 230 with an elastomeric or other type of waterproof sealant, using waterproof materials such as plastic or rubber for the body of the connection pod 230, and by potting any electronic circuitry in the connection pod 230 with a waterproof potting compound, such that if any moisture were to penetrate the body of the connection pod 230, the electronic circuitry inside would not be affected.

As in the shower kit 200 described above with respect to FIG. 2a, the enclosure 250 of the shower kit 200' of FIG. 2b again includes a first aperture 251 through which the removable connector 222 may be inserted to electrically couple the user interface pod 140 to the control unit 120 (where the functionality of the user interface pod 140 is integrated into the control unit 120, such as in the LifeVest® model 4000 Cardioverter Defibrillator, aperture 251 may be omitted). The enclosure 250 also includes a second aperture 252. However in this embodiment, the aperture 252 is dimensioned to receive the end of a cable that is electrically coupled to the connection pod 230 and which includes a removable connector 223' that is similar to the connector 223 used to electrically couple connection pod 130 to the control unit 120 in FIG. 1b. As in the shower kit 200, the first and second apertures 251 and 252 of the enclosure 250 of shower kit 200' may be surrounded by an elastomeric seal that conforms to the diameter of the cable passed therethrough to prevent the ingress of water into the enclosure 250. The enclosure 250 may also include a strap 260 that is attached to the enclosure 250 to permit the enclosure (with control unit 120 sealed therein) to be worn on the patient's body during bathing, or alternatively, to be hung on a hook.

As in the shower kit 200, the shower kit 200' may also include an enclosure 270 in which the user interface pod 140 can be received and protected from moisture, where the user interface pod 140 is not itself water-resistant. Where the wearable medical device 100' includes a user interface pod 140' that is water-resistant or waterproof, or where the functionality of the user interface pod 140, 140' is integrated into the control unit 120, the use of the enclosure 270 may be omitted. As in the shower kit 200, the shower kit 200' includes a plurality of ECG sensing electrodes 212 and a plurality of therapy electrodes 214 which may be of the same type as those described with respect to FIG. 2a. However, in shower kit 200,' these electrodes are directly attached to the connection pod 230, rather than to a mating portion 232b of the connector 232 shown in FIG. 2a.

In accordance with an aspect of the present invention, during those times where the patient is not bathing, the patient may wear the wearable medical device 100' illustrated in FIG. 1b while awake and while asleep. When it is necessary or desirable to bath, the patient may use the shower kit 200' in the following manner to minimize the amount of time during which they are not protected from cardiac arrest. When the patient decides to bathe, the patient removes their clothing, disconnects the connector 222 that is electrically coupled to the user interface pod 140, 140' from the control unit 120 and disconnects the removable connector 223 that is electrically coupled to the connection pod 130 from the control unit 120. The patient may then remove the harness 110 with the connection pod 130 still attached, insert the control unit 120 into the enclosure 250, push the connector 222 through the aperture 251 in the enclosure 250 and electrically couple it to the control unit 120. The patient may then push the connector 223' that is attached to the connection pod 230 through the aperture 252 in the enclosure 250 and connect it to the control unit 120 so that the control unit 120 is electrically coupled to the connection pod 230, the plurality of ECG sensing electrodes 212, and the plurality of therapy electrodes 214. The patient would then typically attach the plurality of ECG sensing electrodes 212 to the front and back and sides of their body, and then attach the therapy electrodes 214a and 214b to the front and back of their body. Although the exact location of the electrodes 212, 214 may vary, they may generally be attached to the patient's body in locations similar to those of the wearable medical device 100'. As described previously with respect to the embodiment of FIG. 2a, the electrodes 212, 214 may be placed in alternative locations on the patient's body where assistance is not available, or where the patient lacks dexterity, and in certain embodiments, the plurality of ECG sensing electrodes 212 may include only a single pair of ECG sensing electrodes. Depending upon whether a water resistant user interface pod 140' or non-water resistant user interface pod 140 was used, the patient may place the non-water resistant user interface pod 140 into the enclosure 270 and seal the enclosure. The enclosure 250 may then be sealed and the patient is now ready to bathe. Because the patient is now protected, they may shower or bathe for as long as they would like, or as frequently as desired.

It should be appreciated that the various steps described above may be performed in an order different than that described above. For example, to further reduce the amount of time the patient is not protected, the patient may get undressed and place the electrodes 212, 214 on their body while the wearable medical device 100' and its associated harness 110 are still in position on the patient's body. As with the first embodiment, the shower kit 200' provides the patient with protection against cardiac arrest while utilizing most of the components of the wearable medical device 100 of FIG. 1a with minimal modification, and with minimal added expense.

Figure 2C:
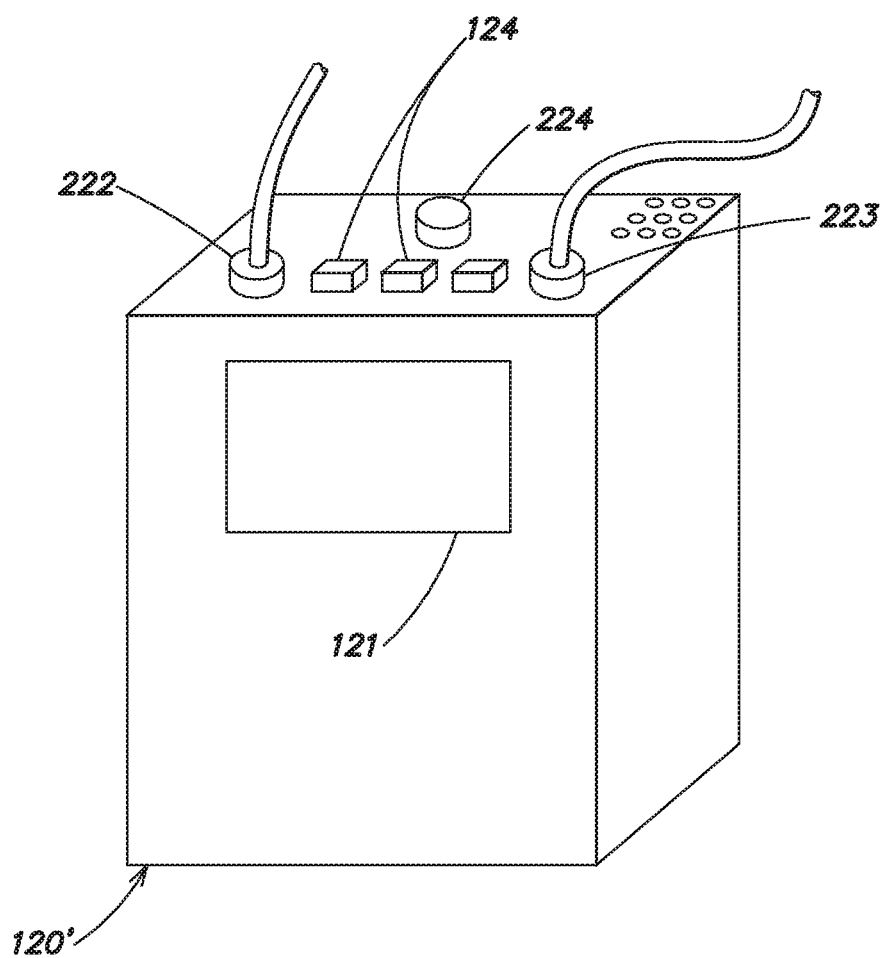
FIG. 2c illustrates an alternative control unit that may be used with a wearable medical device in accordance with an embodiment of the present invention.

FIG. 2c illustrates a control unit 120' in accordance with an alternative embodiment of the present invention that may be used to minimize the amount of time a patient is not protected before and/or after bathing or showering. As shown, the control unit 120' is similar to the control unit 120 described previously with respect to FIG. 1b, in that it includes a display 121, one or more buttons 124, and connection ports to receive removable connectors 222 and 223 (although it should be appreciated that in some embodiments, the connection port to receive removable connector 222 may be omitted where the functionality of the user interface pod 140, 140' is integrated into the control unit 120'). In contrast to previous embodiments, the control unit 120' includes an additional connection port 224 that is configured to mate with the removable connector 223' of the shower kit 200' of FIG. 2b. The connection port 224 permits the removable connector 223' that is connected to the connection pod 230 to be operatively connected to the control unit 120' while the connection pod 130 is still operatively connected to the control unit 120'. While the patient is still wearing and protected by the wearable medical device 100', the patient may remove their clothing, and attach the plurality of ECG sensing electrodes 212 and the plurality of therapy electrodes 214 of the shower kit 200' to their body. The patient can then push the connector 223' that is attached to connection pod 230 through the aperture 252 in the enclosure 250 and connect it to the connection port 224 on the control unit 120'. The patient may then disconnect the connector 223 from the control unit 120' and remove the harness 110 from their body while protected by the electrodes of the shower kit 200'.

In one embodiment, the control unit 120' can include circuitry to detect the connection of connector 223' and connector 223 to the control unit 120' and to automatically switch between using the plurality of ECG sensing electrodes 112 and the plurality of therapy electrodes 114 that are connected to connection pod 130 and using the plurality of ECG sensing electrodes 212 and the plurality of therapy electrodes 214 that are connected to connection pod 230. For example, where the connector 223 is connected to the control unit 120' and the connector 223' is subsequently connected to connection port 224, the control unit 120' can detect that connection and automatically switch from using the plurality of ECG sensing electrodes 112 and the plurality of therapy electrodes 114 that are connected to connection pod 130 to the plurality of ECG sensing electrodes 212 and the plurality of therapy electrodes 214 that are connected to connection pod 230. Where the connector 223 is subsequently disconnected and reconnected to the control unit 120', the control unit 120' can detect that connection and automatically switch from using the plurality of ECG sensing electrodes 212 and the plurality of therapy electrodes 214 that are connected to connection pod 230 to using the plurality of ECG sensing electrodes 112 and the plurality of therapy electrodes 114 that are connected to connection pod 130.

In an alternative embodiment, the control unit 120' may include a user interface routine by which a user can manually select which of the connection ports is active. For example, where connector 223 and connector 223' are both connected to the control unit 120', the user may select which one is to be used and then remove the other connector. After showering or bathing, the patient may dry themselves off, reconnect the connector 223 to the control unit 120', and re-attach the harness 110 in position about their body prior to changing their selection and disconnecting the connector 223'.

In yet a further alternative embodiment, the control unit 120' may include a user interface routine that not only permits a user to select which one of the connection ports is active, but to also permit each of the connection ports to be active simultaneously. This would allow the wearable medical device to be used as a wearable cardioverter defibrillator that is not only capable of monitoring and protecting the patient wearing the wearable medical device, but also permitting the wearable medical device to be used as Automatic External Defibrillator (AED) for another. For example, where the patient wearing the wearable medical device happens upon another person that appears to be suffering a cardiac arrhythmia, the patient may attach the electrodes 212 and 214 of the shower kit 200' to the body of the other person, and connect the connector 223' to the connection port 224 of the control unit 120'. For such use, the wearable medical device may include a pocket or pouch in which the shower kit 200' may be stored. Upon connection of the connector 223' to the connection port 224, the control unit 120' may monitor the ECG signals of both the patient and the other person, and where a shockable cardiac arrhythmia is detected on either the patient or the other person, the control unit 120' may apply a defibrillating shock to that person whose ECG signals correspond to the detected cardiac arrhythmia. It should be appreciated that this embodiment is not limited to the use of a shower kit that includes discrete ECG sensing electrodes 212 and discrete therapy electrodes 214 such as that shown in FIG. 2b, as combined ECG/therapy electrodes (described in more detail below with respect to FIGS. 3a-d) could alternatively be used.

Figure 3C:
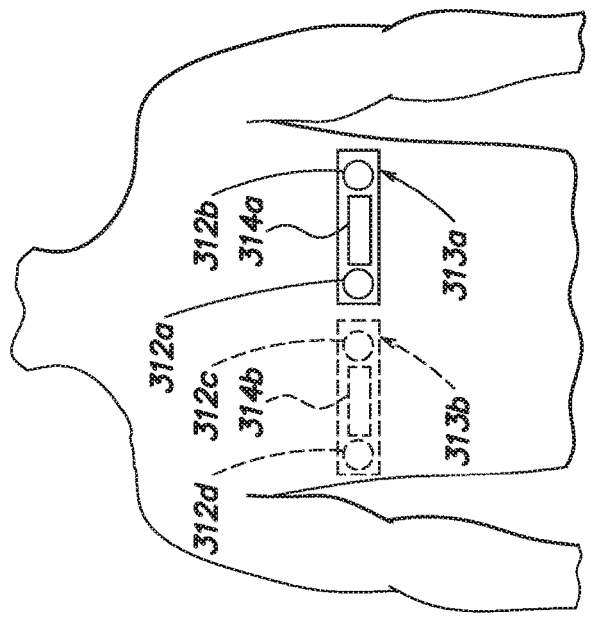
FIG. 3c illustrates the manner in which the ECG/therapy electrode system of FIGS. 3a and 3b may be worn by a patient.

Various alterations may be made to the shower kits 200 and 200' described with respect to FIGS. 2a and 2b. For example, FIGS. 3a-3c illustrate an alternative arrangement of ECG sensing electrodes and therapy electrodes that may be used with a wearable medical device to 100' to provide protection from cardiac arrest during showering or bathing. As shown, rather than including a plurality of discrete ECG sensing electrodes 212 and a plurality of discrete therapy electrodes 214 (FIGS. 2a and 2b), a pair of combined ECG/therapy electrodes 313a, 313b may be used instead. Each combined ECG/therapy electrode 313a, 313b of the pair includes a pair of ECG sensing electrodes 312 and a single therapy electrode 314a or 314b that are disposed on a common adhesive backing 309. The combined ECG/therapy electrodes 313a and 313b are electrically compatible with the plurality of ECG sensing electrodes 112, 212, and the plurality of therapy electrodes 114, 214 of FIGS. 1a, 1b, 2a, and 2b, such that they may be used with the control unit 120 or 120' without modification.

The electrode system 300 of FIG. 3a includes a waterproof connector portion 232b that is electrically coupled to each of the combined ECG/therapy electrodes 313a, 313b and is configured to mate with the connector portion 232a of FIG. 2a. Thus, the electrode system 300 of FIG. 3a may be included in the shower kit 200 and used instead of the electrode system shown in FIG. 2a. The electrode system 301 of FIG. 3b includes a connection pod 230 that is electrically coupled to each of the combined ECG/therapy electrodes 313a, 313b and to a removable connector 223' that is configured to mate with the control unit 120 or 120'. The connection pod 230 and the removable connector 223' may be identical in form and function to those same elements described with respect to FIG. 2b. Thus, the electrode system 301 of FIG. 3b may be included in the shower kit 200' and used instead of the electrode system shown in FIG. 2b.

FIG. 3c illustrates the manner in which the pair of combined ECG/therapy electrodes 313a, 313b may be worn on a patient's body. A first of the combined ECG/therapy electrodes 313a may be adhered to the front of the patient's torso, and the second of the combined ECG/therapy electrodes 313b (shown in dotted line form) adhered to the back of the patient's torso so that the pair of combined ECG/therapy electrodes 313a, 313b provides a front-to-back pair of ECG sensing electrodes 312a, 312c, a side-to-side pair of ECG sensing electrodes 312b, 312d, and front and back therapy electrodes 314a, 314b in a manner similar to that of wearable medical device 100 and 100'. Although not shown in FIG. 3c, it should be appreciated that the pair of combined ECG/therapy electrodes 313a, 313b may be worn on the patient's body in other locations. For example, ECG/therapy electrode 313a may be positioned on one side of the patient's torso with the therapy electrode 314a approximately centered below one armpit, and the other ECG/therapy electrode 313b positioned on the other side of the patient's torso with the therapy electrode 314b approximately centered below the other armpit. Although each of the combined ECG/therapy electrodes 313a, 313b illustrated in FIGS. 3a-3c is shown as including a pair of ECG sensing electrodes 312a, 312b, and 312c, 312d, it should be appreciated that in other embodiments, only a single ECG electrode may be included in each combined ECG/therapy electrode 313a, 313b.

Figure 3D:
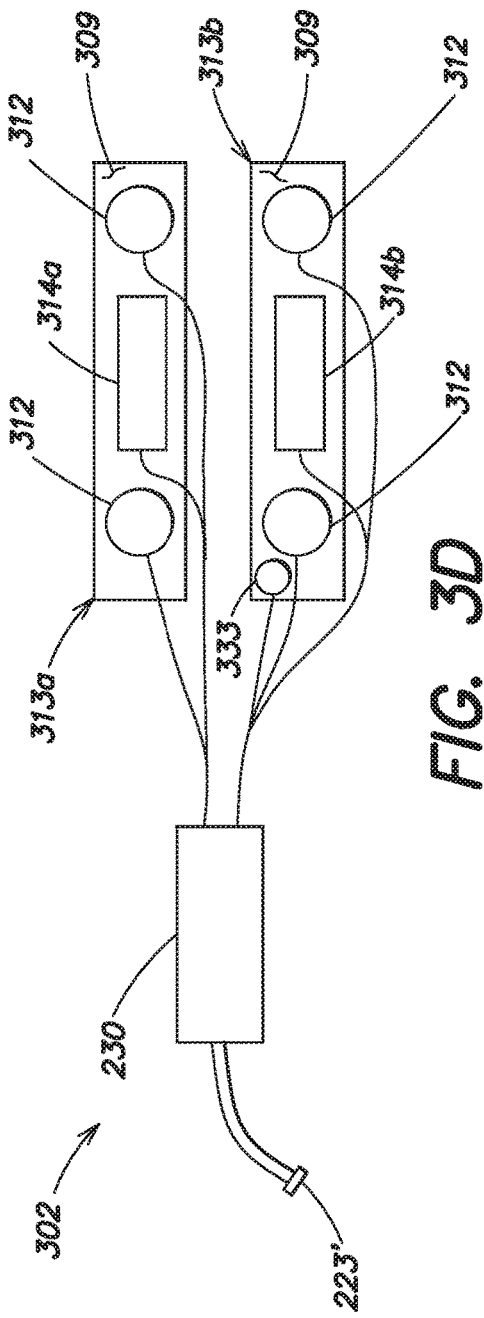
FIG. 3d illustrates a combined ECG/therapy electrode system for use with the shower kit of FIG. 2b in accordance with another embodiment of the present invention.

FIG. 3d illustrates yet an alternative arrangement of ECG sensing electrodes and therapy electrodes that may be used with a wearable medical device to 100' to provide protection from cardiac arrest during showering or bathing. As in the embodiments of FIGS. 3a-3c, this embodiment again includes a pair of combined ECG/therapy electrodes 313a, 313b that may be used instead of the plurality of discrete ECG sensing electrodes 212 and the plurality of discrete therapy electrodes 214 of FIGS. 2a and 2b. Each combined ECG/therapy electrode 313a, 313b of the pair again includes a pair of ECG sensing electrodes 312 and a single therapy electrode 314a or 314b that are disposed on a common adhesive backing 309. However, in this embodiment, at least one of the pair of combined ECG/therapy electrodes 313a, 313b further includes a patient responsiveness button 333 by which the patient can indicate to the control unit 120' that they are conscious in the event of a detected cardiac arrhythmia. This embodiment is particularly well suited for those embodiments in which this functionality is integrated on the control unit 120', rather than on the user interface pod 140, 140'. In the event that a cardiac arrhythmia is detected and the control unit 120' issues a warning that application of a defibrillating shock is imminent, the patient may press and hold the patient responsiveness button 333 to delay or withhold the treatment sequence.

The electrode system 302 of FIG. 3d includes a water resistant and/or waterproof connection pod 230 that is electrically coupled to each of the combined ECG/therapy electrodes 313a, 313b and to a removable connector 223' that is configured to mate with the connection port 224 on the control unit 120'. The connection pod 230 and the removable connector 223' may be similar in form and function to those same elements described with respect to FIG. 2b. In accordance with an aspect of the present invention, the electrode system 302 of FIG. 3d is particularly well suited for use with the control unit 120' described with respect to FIG. 2c, where the connection port 224 need not be identical and backwards compatible with the connection pod 130 and the plurality of ECG sensing electrodes 112 and the plurality of therapy electrodes 114 associated with the harness 110. Thus the connection port 224 may be configured to include the ability to receive a patient responsiveness signal from the patient. The manner in which the pair of combined ECG/therapy electrodes 313a, 313b of the electrode system 302 may be worn on the patient's body is similar to that described above with respect to FIGS. 3a-3d, and thus further discussion is omitted herein.

Figure 3E:
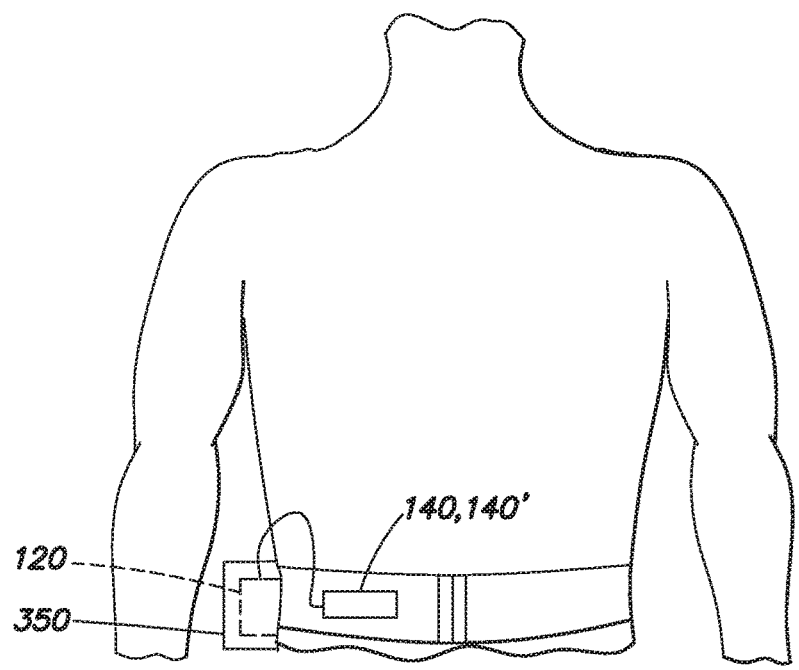
FIGS. 3e and 3f illustrate alternative forms of a water-resistant enclosure that may be associated with the shower kits of FIGS. 2a and 2b.
Figure 3F:
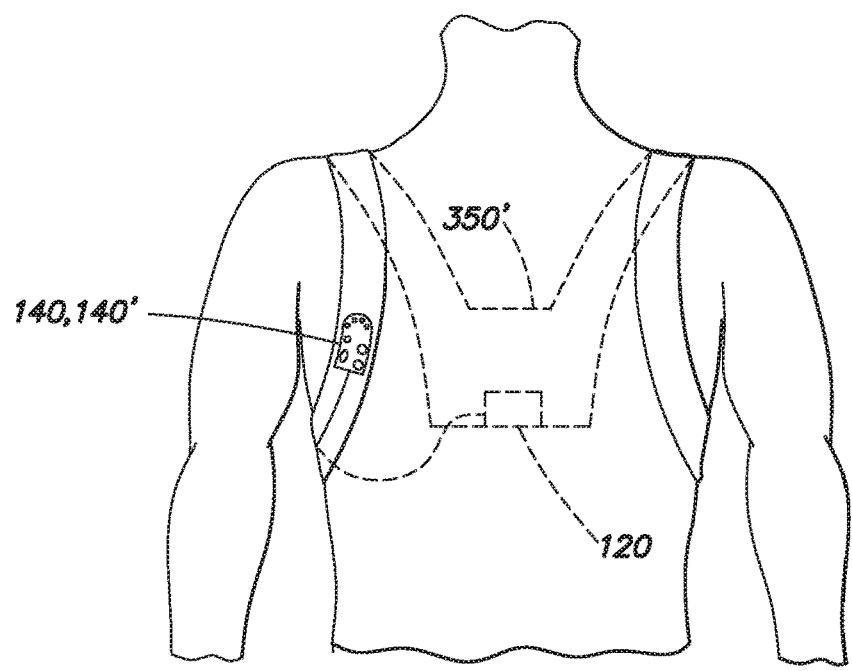

FIGS. 3e and 3f illustrate some additional variations that may be made to the enclosure 250 described with respect to FIGS. 2a and 2b. For example, FIG. 3e illustrates an enclosure 350 in the form of a belt or fanny pack that can be worn by the patient when showering. In this embodiment, the user interface pod 140, 140' may be attached to the belt of fanny pack for convenient access by the patient. FIG. 3f illustrates an alternative embodiment in which the enclosure 350' has the form of a backpack. In this embodiment, the user interface pod 140, 140' may be attached to a shoulder strap of the backpack.

Figure 4A:
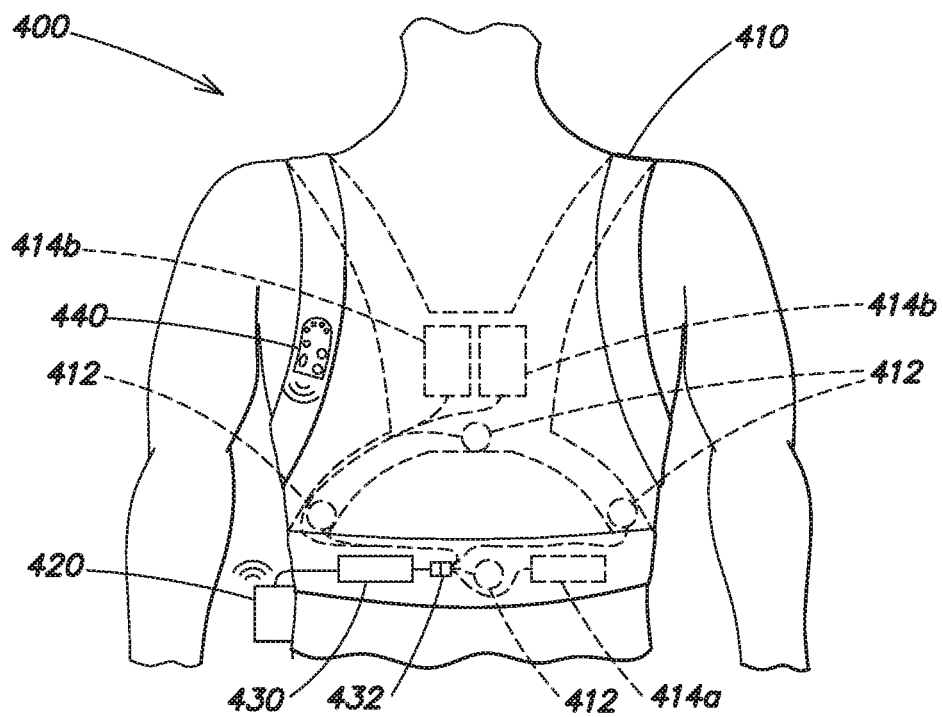
FIG. 4a illustrates a waterproof wearable medical device in accordance with an embodiment of the present invention.

FIG. 4a illustrates a waterproof wearable medical device, such as a wearable defibrillator in accordance with another embodiment of the present invention. The waterproof wearable medical device 400 is generally similar in both form and function to the wearable medical device 100 described with respect to FIG. 1a and the wearable medical device 100' of FIG. 1b. Accordingly, only the differences are described in detail herein. As with the wearable medical devices 100 and 100' of FIGS. 1a and 1b, the waterproof wearable medical device 400 includes a harness 410 having a pair of shoulder straps and a belt that is worn about the torso of the patient. The waterproof wearable medical device 400 also includes a plurality of ECG sensing electrodes 412 and a plurality of therapy electrodes 414 that are electrically coupled to a control unit 420 via a connection pod 430. In accordance with an aspect of the present invention, the harness 410 is formed from a waterproof material such as rubber or Neoprene®, although other water-resistant or waterproof materials may be used. The connection pod 430 is similar in construction to the connection pod 230 described with respect to FIG. 2b, in that it is specifically configured to be waterproof. For example, any openings in the connection pod 430 are sealed with an elastomeric or other type of waterproof sealant, the body of the connection pod 430 is formed from a waterproof material, such as plastic, and any electronic circuitry within the connection pod 430 is potted in a potting compound so as to be unaffected by moisture. The plurality of ECG sensing electrodes 412 and the plurality of therapy electrodes 414 may be similar to those used in the wearable medical device 100' and described with respect to FIG. 1b (e.g., dry-sensing capacitance ECG sensing electrodes and gelled therapy electrodes), or otherwise. Although the plurality of therapy electrodes each preferably include a gel-pack to release an impedance reducing (i.e., electrically conductive) gel when it is determined that one or more defibrillating shocks should be administered to the patient, it should be appreciated that in certain environments, such as in the salt water of the ocean or a salt water pool, the conductivity of the water may itself be sufficient to ensure a low impedance path between the electrodes and the patient's body.

Because waterproof materials such as rubber or Neoprene® do not breathe as well as other materials, the medical device 400 may include a waterproof connector 432, similar to that described with respect to connector 232 of FIG. 1b. The presence of the waterproof connector 432 permits a patient to use the control unit 420 with the harness 410 and associated components of the device 400 when showering, bathing or swimming is desired, and to use the control unit 420 with the harness 110 and associated components of the device 100' of FIG. 1b at other times.

Although the control unit 420 is similar in function to the control units 120, 120' described previously with respect to FIGS. 1-3, it is constructed to be waterproof. In this regard, the body or case of the control unit 420 is formed from a waterproof or water-resistant material, such as plastic and sealed to withstand water. Joints in the body or case of the control unit 420 are sealed with an elastomeric sealant or other type of waterproof sealant, and any openings in the case or body of the control unit 420 (such as the opening in the case where the cable that connects to connection pod 430 exits, or openings for buttons 124 and display 121) are sealed with o-rings or an elastomeric sealant. In further contrast to the wearable medical device described with respect to FIGS. 1a and 1b, the waterproof wearable medical device 400 includes a wireless user interface pod 440 that wirelessly communicates with the control unit 420. In this embodiment, both the wireless user interface pod 440 and the control unit 420 include a wireless RF transceiver that communicate with one another using a wireless communication standard and protocol that is optimized for low cost and shorter distance (e.g., 10 meters) RF communications, such as Bluetooth, Wireless USB, or ZigBee. It should be appreciated that in other embodiments, the wireless user interface pod 440 and the control unit 410 may communicate with one another using communication standards and protocols that are capable of communicating over greater distances, such as Wireless Ethernet, or GSM.

Although the functionality of the wireless user interface pod 440 is similar to that of the user interface pod 140, the wireless user interface pod 440 is also constructed to be waterproof. Thus, for example, the case or body of the wireless user interface pod 440 is formed from a waterproof material such as plastic, and any openings in the case or body are sealed with o-rings or an elastomeric seal. Apertures in the case or body of the wireless user interface pod 420 for a speaker or alarm may be sealed with a water-resistant but sound permeable material, such as GORE-TEX®. The case or body of the wireless user interface pod 440 may include a clip or hook and loop type fastener to permit the user interface pod 440 to be attached to the harness 410.

Figure 4B:
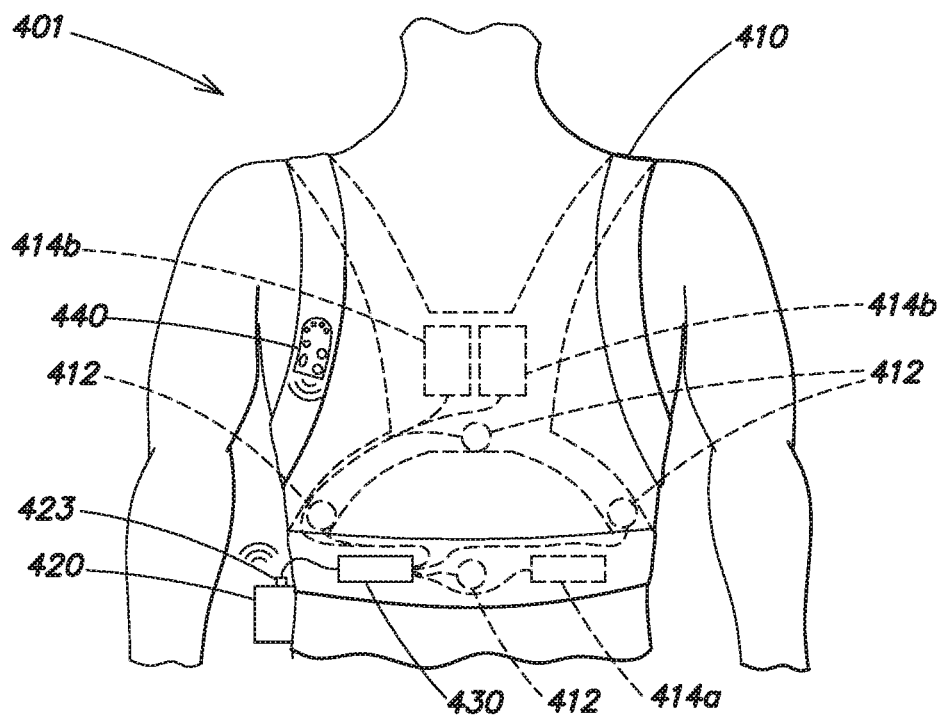
FIG. 4b illustrates a waterproof wearable medical device in accordance with another embodiment of the present invention.

FIG. 4b illustrates a waterproof wearable medical device, such as a wearable defibrillator, in accordance with another embodiment of the present invention. The waterproof wearable medical device 401 is generally similar to the waterproof wearable medical device 400 of FIG. 4a with one exception. Rather than including a removable connector 432 to connect the connection pod 430 to the plurality of ECG sensing electrodes 412 and the plurality of therapy electrodes 414, the device 401 includes a removable and waterproof connector 423 that is similar to the removable connector 223' described with respect to FIG. 2b, but which forms a water-tight seal with the control unit 420. In this embodiment, where the patient desires to shower, bathe, swim, or otherwise immerse themselves in water, they may disconnect the control unit 420 from the connection pod 130 of the harness 110 of the wearable medical device 100' and connect it instead to the connection pod 430.

Figure 4C:
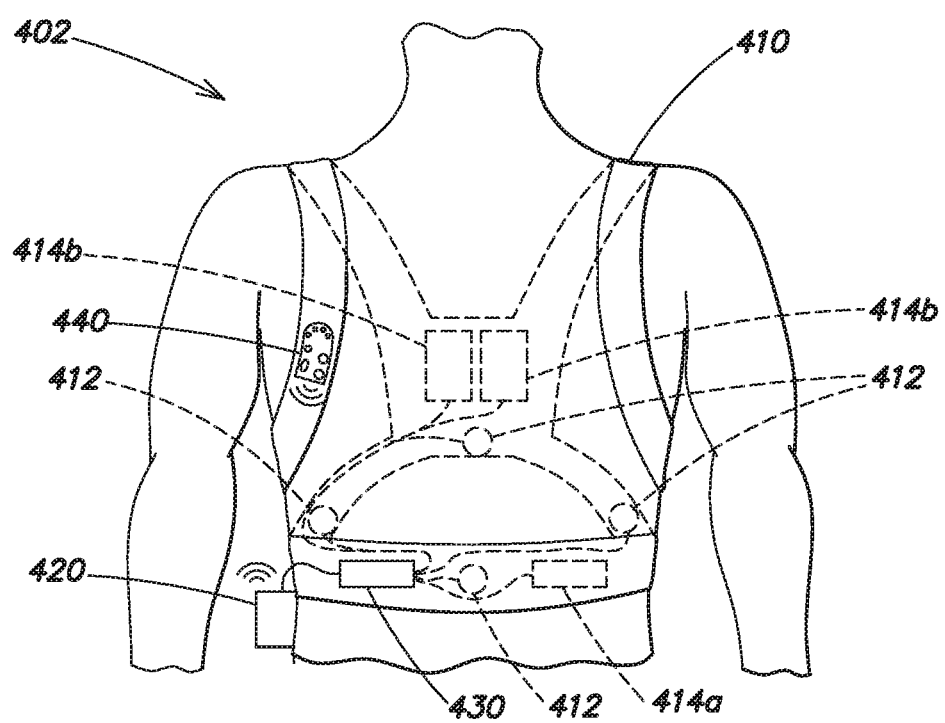
FIG. 4c illustrates a waterproof wearable medical device in accordance with a further embodiment of the present invention.

FIG. 4c illustrates a waterproof wearable medical device, such as a wearable defibrillator, in accordance with yet another embodiment of the present invention. The waterproof wearable medical device 402 is generally similar to the waterproof wearable medical devices 400 and 401 of FIGS. 4a and 4b. However, the waterproof wearable medical device 402 is designed to be worn continuously by the patient, whether awake, asleep, or while showering, bathing, or swimming. As a result, the connection pod 430 is permanently coupled to the control unit 420 and permanently coupled to the plurality of ECG sensing electrodes 412 and the plurality of therapy electrodes 414 in a waterproof manner.

Figure 5A:
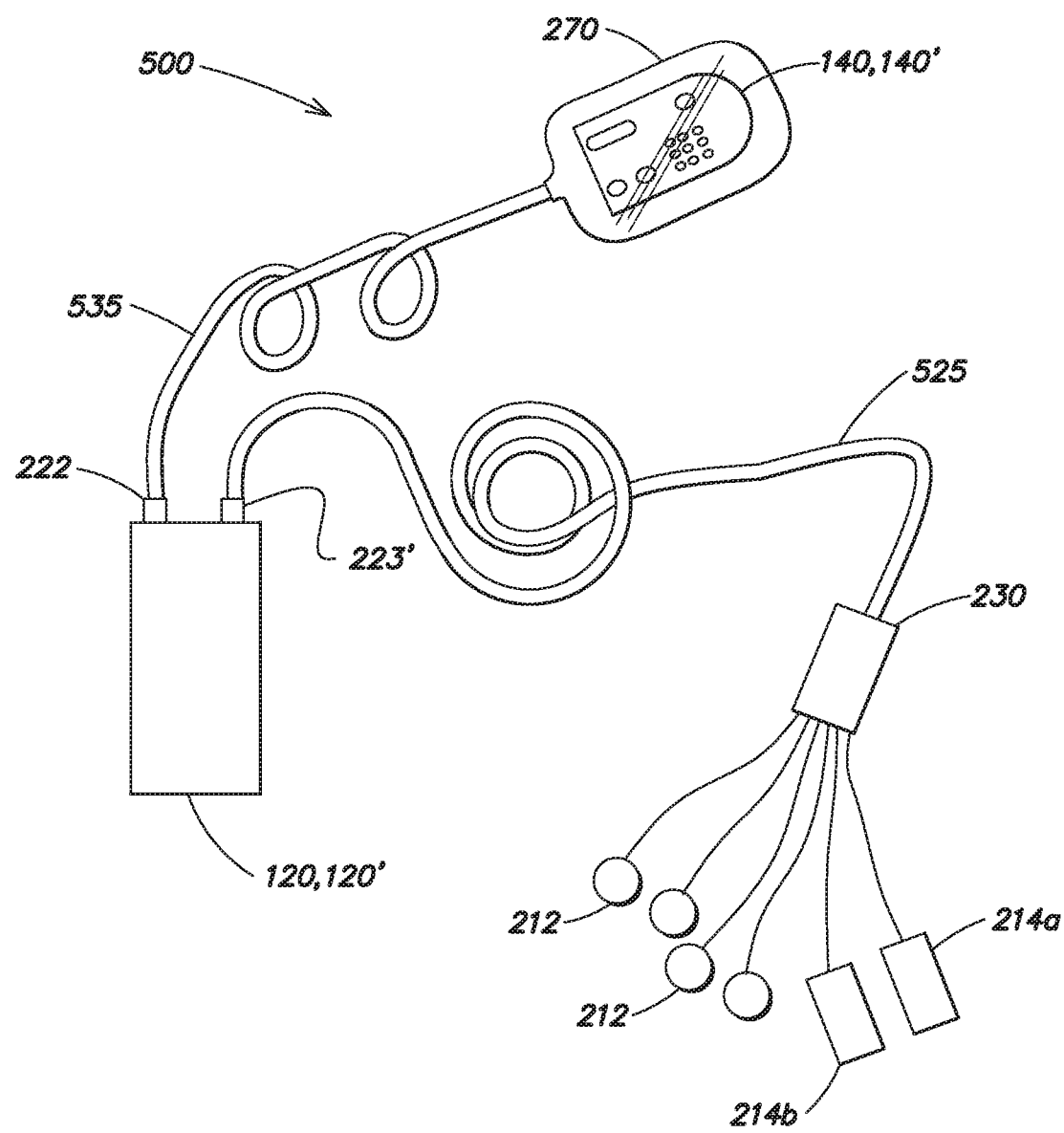
FIG. 5a illustrates a shower kit that may be used with the wearable medical device of FIG. 1b in accordance with another embodiment of the present invention.

FIG. 5a illustrates an alternative shower kit 500 in accordance with an embodiment of the present invention in which those elements of the wearable medical device 100' that could be compromised by contact with water or another liquid, such as control unit 120, may be placed in a secure and dry location while the patient is showering or bathing. The shower kit 500 is similar to the shower kit 200' described with respect to FIG. 2b, in that it includes a plurality of ECG sensing electrodes 212 and a plurality of therapy electrodes 214 which may be similar in construction to the plurality of ECG sensing electrodes 212 and the plurality of therapy electrodes 214 described with respect to FIG. 2b. The shower kit 500 also includes a connection pod 230 that is similar to the connection pod 230 of FIG. 2b and which is constructed to be water resistant and/or waterproof, and a user interface pod 140, 140'. The user interface pod 140, 140' may be a water resistant user interface pod 140' or a non-water resistant user interface pod 140. However, in contrast to the shower kit 200', the cable 525 that electrically couples the connection pod 230 to the control unit 120 and the cable 535 that electrically couples the user interface pod 140, 140' to the control unit 120 are of a sufficient length (e.g., approximately 3 meters or more) to permit the control unit 120 to be placed outside of the shower or bathing area in a dry location, and to remain connected while allowing free movement of the patient, even in the event that the patient falls down (e.g., should the patient experience cardiac arrest). As depicted, the cable 525 has a removable connector 223' that electrically couples the cable 525 to the control unit 120, and the cable 535 has a removable connector 222 that electrically couples the cable 535 to the control unit 120. The connectors 223' and 222 may be identical to the connectors 223' and 222 of FIG. 2b, respectively, and need not be water resistant. Where a non-water-resistant user interface pod 140 is used, enclosure 270 may be used to protect the user interface pod 140 as previously described. It should be appreciated that if the cable 535 that electrically couples the user interface pod 140, 140' to the control unit 120 is not of a sufficient length, a cable extender may be provided. Although the cable extender would need to be of a sufficient length to permit the control unit 120 to remain in a secure and dry location while the patient was showering, this would enable the control unit 120 and the user interface pod 140, 140' of FIG. 1b to be used without modification.

It should be appreciated that the shower kit 500 may also be used with the control unit 120' described above with respect to FIG. 2c. For example, the removable connector 223' can be coupled to the connection port 224 of the control unit 120' while the connector 223 is still operatively coupled to the control unit 120' to minimize the amount of time that the patient is not protected. Although the plurality of ECG sensing electrodes 212 and the plurality of therapy electrodes 214 shown in FIG. 5a are depicted as being discrete electrodes, it should be appreciated that a pair of combined ECG/therapy electrodes, such as those depicted in FIGS. 3a-c, may alternatively be used with an extended length cable 525 and either of control unit 120 or control unit 120'. Where the control unit 120' includes a connection port 224 that is configured to receive a patient responsiveness signal, a combined ECG/therapy electrode system, such as the electrode system 302 of FIG. 3d may similarly be used with an extended length cable to provide ECG sensing electrodes, therapy electrodes, and a patient responsiveness button 333 in a single electrode system.

Figure 5B:
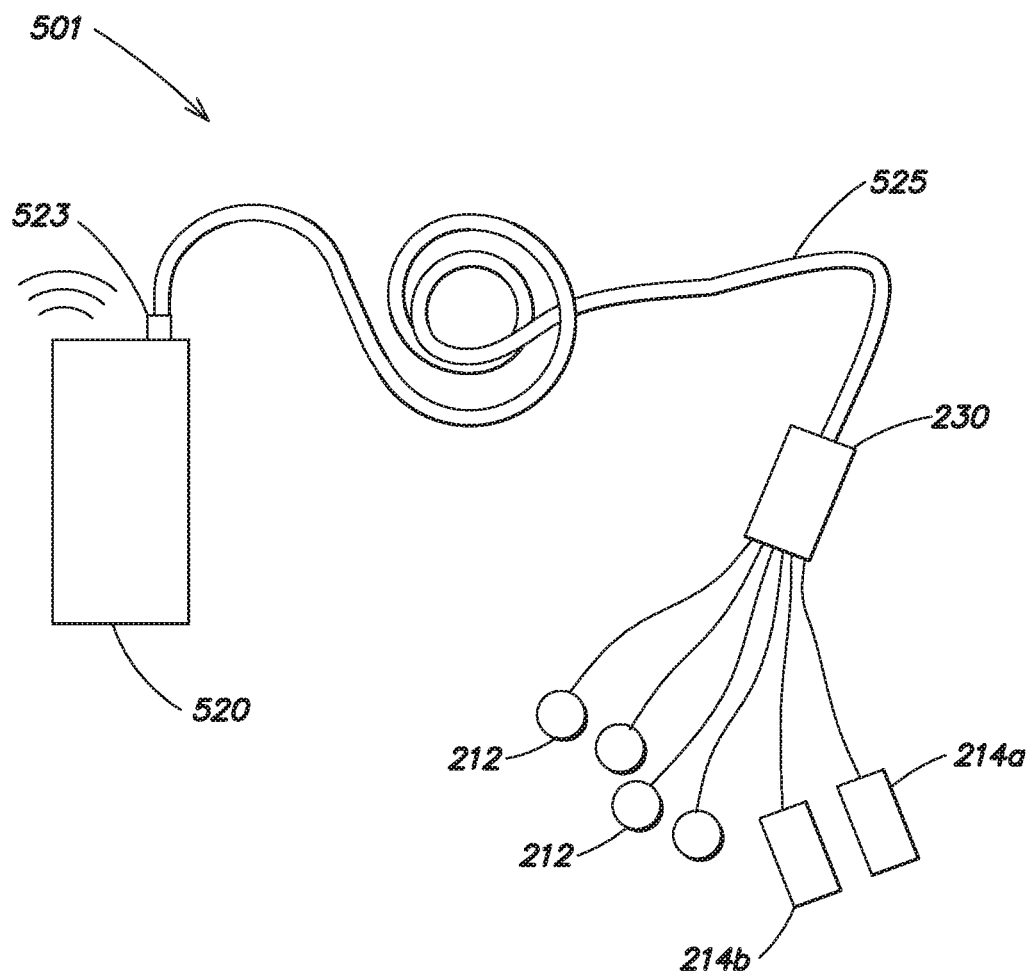
FIG. 5b illustrates a shower kit that may be used with the wearable medical device of FIG. 1b in accordance with a further embodiment of the present invention.

FIG. 5b illustrates an alternative shower kit 501 in accordance with an embodiment of the present invention in which those elements of the wearable medical device which could be compromised by contact with water or another liquid, such as control unit 520, may be placed in a secure and dry location while the patient is showering or bathing. The shower kit 501 is similar to the shower kit 500 described above with respect to FIG. 5a, in that it includes a plurality of ECG sensing electrodes 212 and a plurality of therapy electrodes 214 which may be similar in construction to those described with respect to FIG. 2b. In addition, the shower kit 501 includes a connection pod 230 that is similar to the connection pod 230 of FIG. 2b and is constructed to be water resistant and/or waterproof. As in the shower kit 500, the cable 525 that electrically couples the connection pod 230 to the control unit 520 is of a sufficient length (e.g., approximately 3 meters or more) to permit the control unit 520 to be placed outside of the shower or bathing area in a dry location, and to remain connected while allowing free movement of the patient, even in the event that the patient falls down (e.g., should the patient experience cardiac arrest). As depicted, the cable 525 has a removable connector 523 that electrically couples the cable 525 to the control unit 520.

In the embodiment depicted in FIG. 5*b*, the control unit 520 communicates wirelessly with a wireless user interface pod, such as the waterproof wireless interface pod 440 described with respect to FIGS. 4*a-c*. In other respects, the control unit 520 is similar to the control unit 120 of FIG. 1*b*, and like the control unit 120, need not be waterproof or even water resistant. Although each of the embodiments shown in FIGS. 5*a* and 5*b* is shown as including two pairs of ECG sensing electrodes 212, it should be appreciated that other embodiments may include only a single pair of ECG sensing electrodes 212. Moreover, although the plurality of ECG sensing electrodes 212 and the plurality of therapy electrodes 214 are shown in FIG. 5*b* as being discrete electrodes, it should be appreciated that a pair of combined ECG/therapy electrodes such as those depicted in FIGS. 3*a-c* may alternatively be used.

Figure 6A:
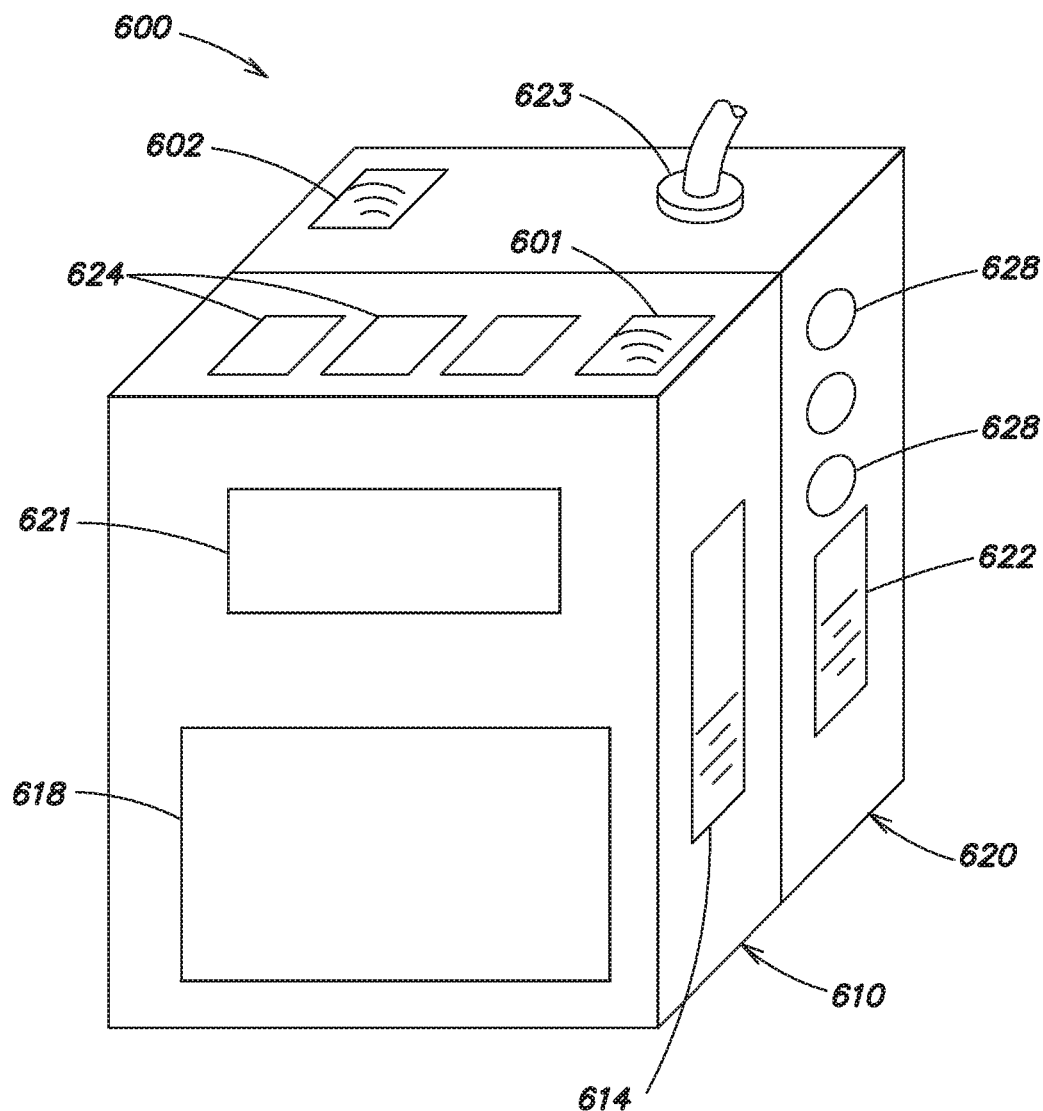
FIG. 6a illustrates a control unit for use with a wearable medical device in accordance with another embodiment of the present invention.

FIG. 6*a* illustrates a control unit in accordance with a further aspect of the present invention. Although the overall functionality of the control unit 600 is similar to that of the control units 120, 120', 420, and 520 described above, that functionality is divided among different and separable units including a first master control unit 610 and a second slave control unit 620. As will be described in further detail below, the master control unit 610 is not intended for use in wet environments, such as a shower or bath, whereas the slave control unit 620 is. For use in a wet environment, the master control unit 610 may be separated from the slave control unit 620 and left in a secure and dry environment, while the slave control unit 620 remains with the patient to protect them in the event of cardiac arrest.

The master control unit 610 includes circuitry 618 that implements the main user interface for the control unit 600 and controls such aspects as the touch screen display 621 and the user interface buttons 624. The circuitry 618 in the master control unit 610 also handles the primary functions of arrhythmia detection and cardiac event recording for the control unit 600. The master control unit 610 further includes a main rechargeable battery pack 614 that provides power to the control unit 600, and powers both the master control unit 610 and the slave control unit 620 when the two are interconnected. The master control unit 610 includes a wireless communication interface 601 for wirelessly communicating with the slave control unit 620 when the two units are physically separated from one another. The wireless interface 601 may also be used to communicate with a wireless user interface pod, such as the wireless user interface pod 440 described above with respect to FIGS. 4*a-c*.

The slave control unit 620 includes capacitors 628 for generating and storing a defibrillating charge, high voltage charging circuitry (not shown) for charging the capacitors 628, and circuitry for controlling the delivery of one or more defibrillating shocks to the patient. The slave control unit 620 also includes a smaller, rechargeable battery 622 that provides power to the slave control unit 620 during those periods of time where the slave control unit 620 is separated from the master control unit 610. In certain embodiments, the battery 622 may be capable of charging the capacitors 628 to a voltage sufficient to provide at least one defibrillating shock. The slave control unit 620 may also include a removable and waterproof connector 623 that is similar in design and function to the connector 423 described previously with respect to FIG. 4*b*. The slave control unit 620 is purposefully designed to be waterproof and includes a wireless communication interface 602 for communicating with the master control unit 610 when the two units are physically separated. The wireless communication interfaces 601, 602 may support any bi-directional wireless communication standard and protocol, including but not limited to wireless USB, wireless Ethernet, ZigBee, Bluetooth, GSM, etc.

Figure 6B:
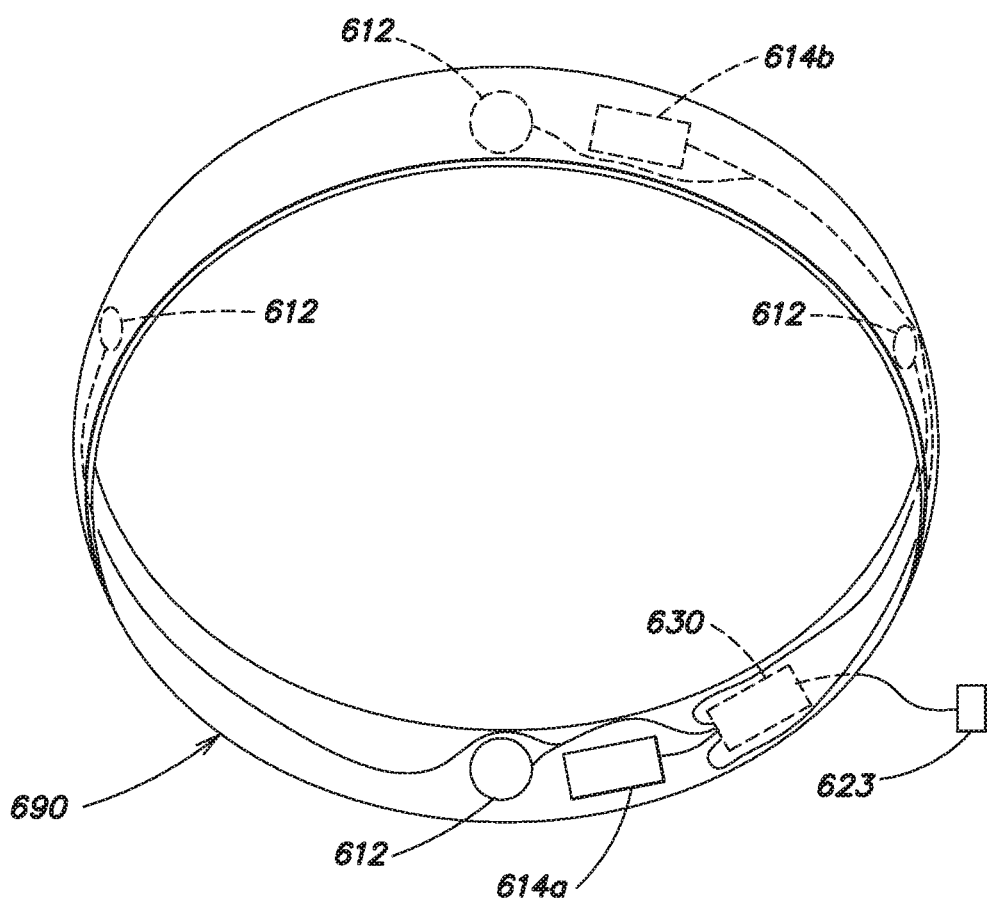
FIG. 6b illustrates a shower belt that may be used with the control unit of FIG. 6a in accordance with another aspect of the present invention.

During operation in generally dry environments, the control unit 600 would typically be connected to a harness similar to the harness 110 depicted in FIG. 1*b*, and both the master control unit 610 and the slave control unit 620 would be coupled together and operate as a single control unit. However, where the patient desires to shower or bathe, the patient would remove the harness 110 and don a shower belt, such as the shower belt 690 illustrated in FIG. 6*b*. The shower belt 690 is completely waterproof and contains all the system elements needed to function as a stand-alone wearable defibrillator. For example, the shower belt 690 includes a plurality of ECG sensing electrodes 612, front and back therapy electrodes 614*a*, 614*b*, a waterproof connection pod 630 which may be similar to the waterproof connection pods 230 and 430 described previously, and a waterproof removable connector 623. The waterproof removable connector 623 may be similar to the removable connector 423 described previously with respect to FIG. 4*b*. Although not shown, the shower belt 690 may include a simplified user interface that is integrated into the belt 690 (e.g., to allow the patient to indicate that they are conscious in response to a detected cardiac arrhythmia), or alternatively, a wireless user interface pod such as the wireless user interface pod 440 described previously with respect to FIGS. 4*a-c* may be used.

After disconnecting the connection pod 130, removing the harness 110, and donning the belt 690, the patient would connect the connector 623 on the belt 690 to the slave control unit 620 and separate the master control unit 610 from the slave control unit 620. The slave control unit 620 may then be attached to the belt 690, so that all elements needed to operate as a stand-alone wearable medical defibrillator system are located on the belt 690 that is attached to the patient's torso. In some embodiments, the belt 690 may include a pocket to receive the slave control unit 620 to again operate as a stand-alone wearable medical defibrillator. During operation, the slave control unit 620 wirelessly communicates with the master control unit 610 which is located in a dry and secure environment (e.g., outside of the shower). Where the master control unit 610 detects arrhythmia and determines that a defibrillating shock should be delivered, the master control unit 610 sends a message to the slave control unit 620 to charge the capacitors 628 via the battery 622. Once the capacitors 628 are charged to the appropriate level, the slave control unit 620 controls the delivery of the defibrillating shock.

It should be appreciated that the slave control unit 620 may include additional circuitry to allow it to protect the patient in the event that communication with the master control unit 610 is not possible. For example, the slave control unit 620 may include circuitry to perform ECG monitoring and arrhythmia detection, as well as capacitor charging and defibrillating shock delivery. Such circuitry may be in addition to the circuitry contained in the master control unit 610. In an alternative embodiment, and in accordance with the teachings of the '096 application, the slave control unit 620 can include circuitry capable of performing all critical functions of the wearable medical device including the monitoring of ECG information, the detection of cardiac abnormalities, and the circuitry for generating and delivering one or more defibrillating shocks to the body of the patient. In this embodiment, the master control unit 610 would be responsible for non-critical functions, such as event recording, storage, and analysis, remote communication capabilities, full featured user interface support, etc.

As discussed above, in the control unit 600, the slave control unit 620 includes a rechargeable battery 622 that provides power to the slave control unit 620 during those periods of time in which it is separated from the master control unit 610. That rechargeable battery 622 may be capable of charging the capacitors 628 to a voltage sufficient to provide at least one defibrillating shock. However, the ability to charge the capacitors 628 to such a voltage level may require a larger and more powerful battery than would otherwise be needed to simply power the circuitry of the slave control unit, thereby increasing the weight of the slave control unit 620.

In accordance with a further aspect of the present invention, the control unit 600 may include the ability to charge the capacitors 628 to a voltage level sufficient to provide at least one defibrillating shock prior to separation of the master control unit 610 and the slave control unit 620. Such a 'shower' mode may be selected by the patient via the user interface of the control unit 600. Once the capacitors 628 are fully charged, the units may be separated from one another and the slave control unit 620 attached to the belt 690. After the patient has finished showering or bathing and the master control unit 610 is reattached to the slave control unit 620, the capacitors can be discharged. This ability to pre-charge the capacitors 628 permits a smaller, lighter weight battery to be used in the slave control unit 620, thereby making it more portable.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A wearable medical device, comprising:
   a water-resistant harness to be worn by a patient;
   a plurality of ECG sensing electrodes disposed on the water-resistant harness and configured to sense an ECG signal of the patient;
   a plurality of therapy electrodes additionally disposed on the water-resistant harness and configured to provide at least one defibrillating biphasic shock to the patient, a first phase of the at least one defibrillating biphasic shock with a first therapy electrode with a second therapy electrode acting as a return, and a second phase of the at least one defibrillating biphasic shock with the second therapy electrode with the first therapy electrode acting as the return,
   wherein the water-resistant harness is configured to dispose the first therapy electrode and the second therapy electrode on opposite sides of the patient's torso;
   a control unit, electrically coupled to the plurality of ECG sensing electrodes and the plurality of therapy electrodes and configured to
      monitor ECG information of the patient based on the sensed ECG signal, and
      responsive to detection of a cardiac arrhythmia in the ECG information of the patient, provide the at least one defibrillating biphasic shock, wherein the control unit is comprised within a waterproof case; and
   a water-resistant or waterproof connection pod configured to electrically couple to the plurality of ECG sensing electrodes, the plurality of therapy electrodes, and the control unit, wherein the connection pod provides the sensed ECG signal from the plurality of ECG sensing electrodes as the ECG information to the control unit and the at least one defibrillating biphasic shock from the control unit to the plurality of therapy electrodes.

2. The device of claim 1, wherein the connection pod comprises ECG signal acquisition circuitry configured to receive the sensed ECG signal and provide a processed ECG signal as the ECG information to the control unit.

3. The device of claim 1, wherein the connection pod comprises a plurality of differential amplifiers configured to receive ECG signals from different ones of the plurality of ECG sensing electrodes.

4. The device of claim 3, wherein the connection pod is configured to provide a differential ECG signal to the control unit based on a difference between the received ECG signals.

5. The device of claim 1, wherein a body of the water-resistant or waterproof connection pod is formed from a waterproof material.

6. The device of claim 5, wherein openings in the body of the water-resistant or waterproof connection pod are sealed with a waterproof sealant.

7. The device of claim 1, wherein the water-resistant or waterproof connection pod comprises electronic circuitry that is potted with a waterproof potting compound.

8. The device of claim 1, wherein the water-resistant or waterproof connection pod further comprises a motion sensor configured to sense patient activity.

9. The device of claim 1, wherein the water-resistant or waterproof connection pod is attached to the water-resistant harness.

10. The device of claim 1, wherein the water-resistant or waterproof connection pod is electrically coupled to the plurality of ECG sensing electrodes and the plurality of therapy electrodes via a water-resistant or waterproof connector.

11. The device of claim 1, wherein the control unit is configured to instruct the patient to press and hold a patient responsiveness button on the control unit to indicate that the patient is conscious, thereby instructing the control unit to withhold delivery of the at least one defibrillating biphasic shock.

12. The device of claim 1, further comprising at least one additional sensor coupled to the control unit, the at least one additional sensor capable of measuring at least one of heart sounds, thoracic impedance, pulse oxygen level, respiration rate, or activity level.

13. The device of claim 1, wherein the waterproof case is formed of a water-resistant or waterproof material comprising plastic.

14. The device of claim 1, wherein joints of the waterproof case are sealed to prevent ingress of water during operation of the device in a wet environment.

15. The device of claim 1, further comprising one or more openings in the waterproof case, wherein the one or more openings are sealed to prevent ingress of water during operation of the device in a wet environment.

16. The device of claim 15, wherein the one or more openings are sealed with O-rings or an elastomer sealant.

17. The device of claim 1, wherein a water resistant material of the water-resistant harness comprises rubber or neoprene.

18. The device of claim 1, further comprising a user interface pod operatively coupled to the control unit, wherein the user interface pod is configured to be handheld or releasably attached to a clothing of the patient or the water-resistant harness.

19. The device of claim 18, wherein the user interface pod comprises a patient responsiveness button by which the patient can indicate that the patient is conscious, thereby instructing the control unit to withhold delivery of the at least one defibrillating biphasic shock.

20. The device of claim 18, wherein the user interface pod is configured to wirelessly communicate with the control unit.

* * * * *